(12) United States Patent
Hamada et al.

(10) Patent No.: US 11,324,474 B2
(45) Date of Patent: May 10, 2022

(54) MEDICAL IMAGE DIAGNOSTIC SYSTEM AND RADIATION DOSE MANAGEMENT APPARATUS

(71) Applicant: CANON MEDICAL SYSTEMS CORPORATION, Otawara (JP)

(72) Inventors: Yuji Hamada, Tustin, CA (US); Naoki Sugihara, Nasushiobara (JP); Manabu Teshigawara, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 122 days.

(21) Appl. No.: 16/570,508

(22) Filed: Sep. 13, 2019

(65) Prior Publication Data

US 2020/0085401 A1  Mar. 19, 2020

(30) Foreign Application Priority Data

Sep. 13, 2018 (JP) .............................. JP2018-171233

(51) Int. Cl.
*A61B 6/00* (2006.01)
*A61B 6/03* (2006.01)

(52) U.S. Cl.
CPC .............. *A61B 6/542* (2013.01); *A61B 6/032* (2013.01); *A61B 6/4057* (2013.01); *A61B 6/461* (2013.01); *A61B 6/463* (2013.01); *A61B 6/467* (2013.01); *A61B 6/545* (2013.01); *A61B 6/037* (2013.01)

(58) Field of Classification Search
CPC ......... G01N 2223/30; G01N 2223/316; G01N 2223/32; G01N 2291/015; G01T 1/29; G01T 1/2921; G01T 1/295; G02B 21/0036; G02B 21/004; G02B 21/0044; G02B 2207/129; G21K 1/00; G21K 1/02; G21K 1/025; G21K 1/04; G21K 1/046; G21K 1/10; G21K 2201/00; A61B 6/06; A61B 6/40; A61B 6/4035; A61B 6/405; A61B 2560/00; A61B 2560/04; A61B 2560/06

See application file for complete search history.

(56) References Cited

U.S. PATENT DOCUMENTS

| | | | |
|---|---|---|---|
| 7,804,936 B2 * | 9/2010 | Pouliot | A61B 6/5282 378/65 |
| 7,835,500 B2 * | 11/2010 | Fu | G06T 7/32 378/128 |
| 8,044,359 B2 * | 10/2011 | Simon | A61N 5/1071 250/370.07 |
| 9,336,591 B2 * | 5/2016 | Mallya | G06T 7/0012 |
| 2012/0051522 A1 * | 3/2012 | Nishino | A61B 6/4411 378/108 |
| 2016/0089101 A1 * | 3/2016 | Lou | A61B 6/40 378/16 |

FOREIGN PATENT DOCUMENTS

| | | |
|---|---|---|
| JP | 2014-151007 A | 8/2014 |
| JP | 2015-43853 A | 3/2015 |

* cited by examiner

*Primary Examiner* — Anastasia Midkiff
(74) *Attorney, Agent, or Firm* — Oblon, McClelland, Maier & Neustadt, L.L.P.

(57) ABSTRACT

A medical image diagnostic system according to an embodiment includes processing circuitry configured to acquire first information related to an exposure dose of a subject by a radioactive agent administered to the subject, and display reference information for determining imaging conditions of X-ray CT imaging to be performed with respect to the subject on a display, based on the first information and second information related to a reference dose.

21 Claims, 11 Drawing Sheets

MEDICAL IMAGE DIAGNOSTIC SYSTEM AND RADIATION DOSE MANAGEMENT APPARATUS

CROSS-REFERENCE TO RELATED APPLICATIONS

This application is based upon and claims the benefit of priority from Japanese Patent Application No. 2018-171233, filed on Sep. 13, 2018, the entire contents of all of which are incorporated herein by reference.

FIELD

Embodiments described herein relate generally to a medical image diagnostic system and a radiation dose management apparatus.

BACKGROUND

Conventionally, a medical image diagnostic apparatus may have a function of managing radiation dose information such as effective dose, absorbed dose, and exposed dose. Further, a general X-ray CT apparatus may have a function of displaying a warning text when an imaging condition exceeding a certain radiation dose is selected before exposure, a function of limiting exposure by a person having no authority by making the person input a password, and the like.

DETAILED DESCRIPTION

A medical image diagnostic system comprises processing circuitry. The processing circuitry is configured to acquire first information related to an exposure dose of a subject by a radioactive agent administered to the subject. The processing circuitry is configured to display reference information for determining imaging conditions of X-ray CT imaging to be performed with respect to the subject on a display, based on the first information and second information related to a reference dose.

Embodiments of the medical image diagnostic system will be described below in detail with reference to the accompanying drawings. The embodiments are not limited to those described below. Further, in principle, the contents described in one embodiment are similarly applicable to other embodiments.

Figure 1:
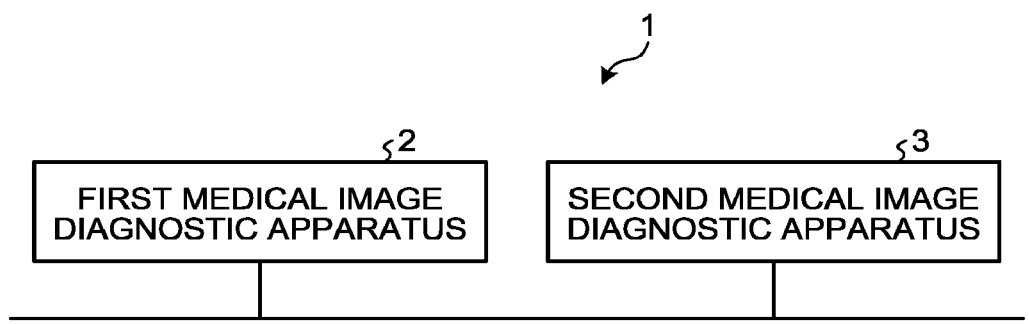
FIG. 1 is a block diagram illustrating a configuration example of a medical image diagnostic system according to embodiments of the present invention.

FIG. 1 is a block diagram illustrating a configuration example of a medical image diagnostic system 1 according to embodiments of the present invention. As illustrated in FIG. 1, the medical image diagnostic system 1 according to the embodiments includes a first medical image diagnostic apparatus 2 related to radiation and a second medical image diagnostic apparatus 3 related to radiation. The first medical image diagnostic apparatus 2 and the second medical image diagnostic apparatus 3 can communicate with each other, for example, via an in-hospital LAN (Local Area Network) or the like.

The first medical image diagnostic apparatus 2 herein is, for example, a PET (Positron Emission Tomography) apparatus, a SPECT (Single Photon Emission Computed Tomography) apparatus, an X-ray CT (Computed Tomography) apparatus, or an X-ray diagnostic apparatus. The second medical image diagnostic apparatus 3 is, for example, a PET apparatus, a SPECT apparatus, an X-ray CT apparatus, or an X-ray diagnostic apparatus. In the medical image diagnostic system 1 according to the embodiments, imaging by the second medical image diagnostic apparatus 3 is performed following imaging by the first medical image diagnostic apparatus 2. In the medical image diagnostic system 1, the combination of the type of the first medical image diagnostic apparatus 2 and the type of the second medical image diagnostic apparatus 3 can be set arbitrarily.

In a first embodiment, the medical image diagnostic system 1 in which the first medical image diagnostic apparatus 2 is a PET apparatus, and the second medical image diagnostic apparatus 3 is an X-ray CT apparatus is described. In the following descriptions, after descriptions of the PET apparatus, the X-ray CT apparatus is described.

The PET apparatus according to the first embodiment receives imaging conditions from an operator, and performs scan of a subject based on the received imaging conditions. More specifically, the PET apparatus receives the type of radioactive agent to be injected, an injection dose, and a residence time of the radioactive agent from the operator, to perform the scan of the subject.

Figure 2:
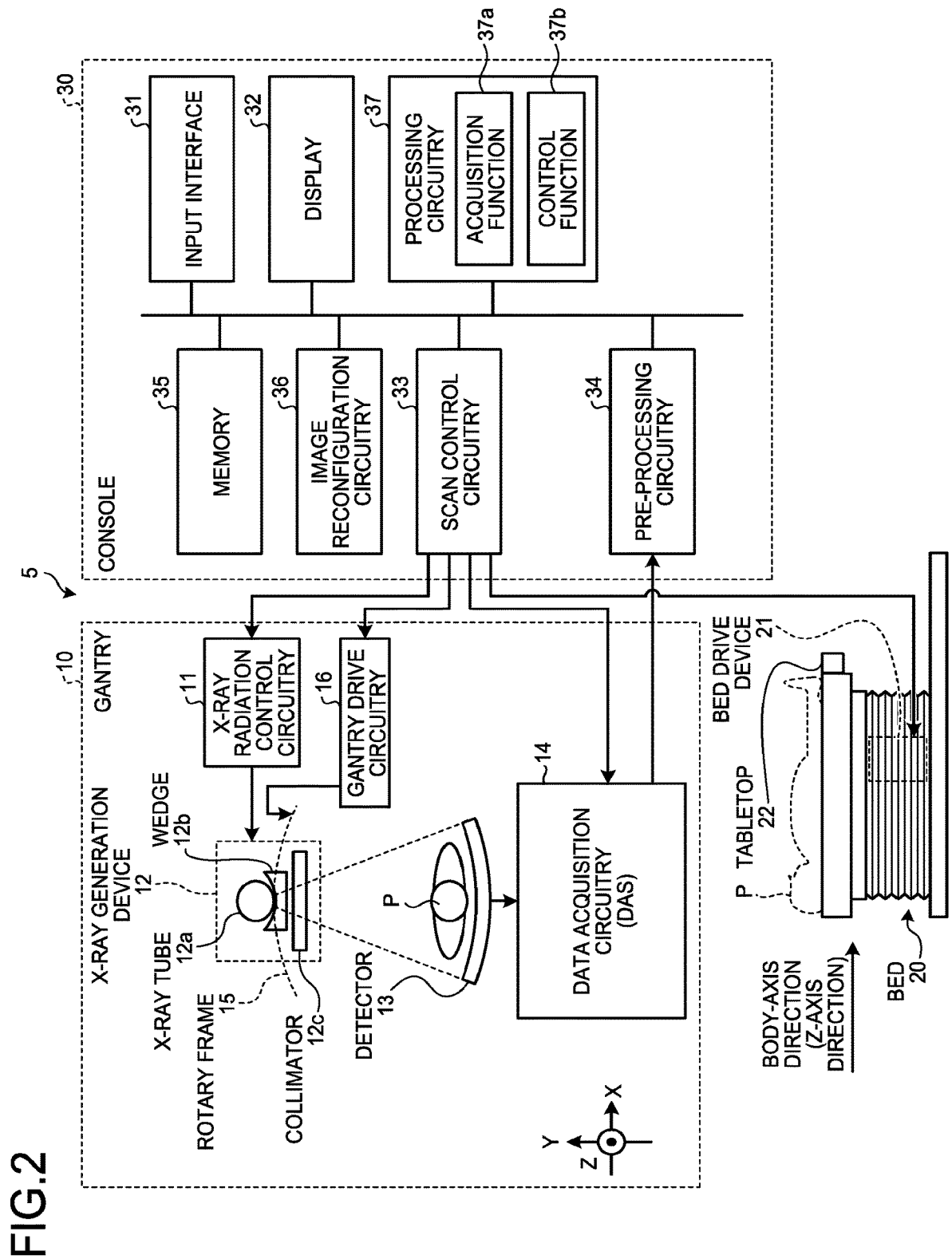
FIG. 2 is a block diagram illustrating a configuration example of an X-ray CT apparatus according to a first embodiment.

FIG. 2 is a block diagram illustrating a configuration example of an X-ray CT apparatus 5 according to the first embodiment. As illustrated in FIG. 2, the X-ray CT apparatus 5 according to the first embodiment includes a gantry 10, a bed 20, and a console 30.

The gantry 10 is a apparatus that emits X rays to a subject P (patient) to detect X rays having transmitted through the subject P and outputs the detected X rays to the console 30. The gantry 10 includes X-ray radiation control circuitry 11, an X-ray generation device 12, a detector 13, data acquisition circuitry (DAS: Data Acquisition System) 14, a rotary frame 15, and gantry drive circuitry 16. As illustrated in FIG. 1, an orthogonal coordinate system formed of an X axis, a Y axis, and a Z axis is defined in the gantry 10. That is, the X axis indicates a horizontal direction, the Y axis indicates a vertical direction, and the Z axis indicates a direction of the central axis of rotation of the rotary frame 15 when the gantry 10 is in a non-tilted state.

The rotary frame 15 is an annular frame that supports the X-ray generation device 12 and the detector 13 so as to be opposed to each other with the subject P being placed therebetween, and rotates at a high speed on a circular path around the subject P by the gantry drive circuitry 16 described later.

The X-ray radiation control circuitry 11 is a device that supplies a high voltage to an X-ray tube 12a as a high-voltage generation unit, and the X-ray tube 12a generates X rays by using the high voltage supplied from the X-ray radiation control circuitry 11. The X-ray radiation control circuitry 11 adjusts the X-ray dosage to be applied to the subject P by adjusting a tube voltage and a tube current to be supplied to the X-ray tube 12a under control of scan control circuitry 33 described later.

Further, the X-ray radiation control circuitry 11 performs switching of a wedge 12b. The X-ray radiation control circuitry 11 also adjusts a radiation range of X rays (a fan angle and a cone angle) by adjusting an aperture of a collimator 12c. The present embodiment can be also applied to a case in which a plurality of types of wedges are manually switched by an operator.

The X-ray generation device 12 is a device that generates X rays and emits the generated X rays to the subject P, and includes the X-ray tube 12a, the wedge 12b, and the collimator 12c.

The X-ray tube 12a is a vacuum tube that emits X-ray beams to the subject P by the high voltage supplied from a high-voltage generation unit (not illustrated), and emits X-ray beams to the subject P with the rotation of the rotary frame 15. The X-ray tube 12a generates X-ray beams that flare with a fan angle and a cone angle. The X-ray tube 12a can continuously emit X rays around the entire perimeter of the subject P for full reconfiguration or can continuously emit X rays in a half reconfigurable exposure range (180 degrees+fan angle) for half reconfiguration, for example, under control of the X-ray radiation control circuitry 11. Further, the X-ray tube 12a can emit X rays (pulsed X rays) intermittently at a preset position (a tube position) under control of the X-ray radiation control circuitry 11. Further, the X-ray radiation control circuitry 11 can modulate the intensity of X rays emitted from the X-ray tube 12a. For example, the X-ray radiation control circuitry 11 increases the intensity of X rays emitted from the X-ray tube 12a at a certain tube position, and decreases the intensity of X rays emitted from the X-ray tube 12a in a range other than the certain tube position.

The wedge 12b is an X-ray filter for adjusting the X-ray dosage of X rays emitted from the X-ray tube 12a.

Specifically, the wedge 12b is a filter that transmits and attenuates X rays emitted from the X-ray tube 12a so that the X rays applied to the subject P from the X-ray tube 12a have a predefined distribution. For example, the wedge 12b is a filter obtained by processing aluminum so as to have a predetermined target angle and a predetermined thickness. The wedge is also referred to as "wedge filter" or "bow-tie filter".

The collimator 12c is a slit for narrowing down the radiation range of X rays with the X-ray dosage being adjusted by the wedge 12b, under control of the X-ray radiation control circuitry 11 described later.

The gantry drive circuitry 16 rotates the rotary frame 15 to turn the X-ray generation device 12 and the detector 13 on the circular path around the subject P.

The detector 13 is a two-dimensional array detector (a plane detector) that detects X rays having transmitted through the subject P, in which detection element columns obtained by arranging X-ray detection elements for a plurality of channels are arranged in a plurality of columns along a body-axis direction (the z-axis direction in FIG. 1) of the subject P. Specifically, the detector 13 according to the first embodiment has X-ray detection elements arranged in multiple columns such as 320 columns along the body-axis direction of the subject P, and can detect X rays having transmitted through the subject P in a wide range, for example, in a range including the lung and the heart of the subject P.

The data acquisition circuitry 14 is a DAS and acquires projection data from the detection data of X rays detected by the detector 13. For example, the data acquisition circuitry 14 performs amplification processing, A/D conversion processing, sensitivity correction processing between channels, and the like with respect X-ray intensity distribution data detected by the detector 13 to generate projection data and transmits the generated projection data to the console 30 described later. For example, when X rays are continuously emitted from the X-ray tube 12a while the rotary frame 15 is being rotated, the data acquisition circuitry 14 acquires a projection data group for the entire perimeter (for 360 degrees). Further, the data acquisition circuitry 14 transmits the acquired respective pieces of projection data to the console 30 described later in association with tube positions. The tube position is information indicating a projection direction of the projection data. The sensitivity correction processing between channels can be performed by pre-processing circuitry 34 described later.

The bed 20 is a apparatus on which the subject P is placed, and as illustrated in FIG. 2, includes a bed drive device 21 and a tabletop 22. The bed drive device 21 moves the tabletop 22 in the Z-axis direction, to move the subject P into the rotary frame 15. The bed drive device 21 can move the tabletop 22 also in the X-axis direction. The tabletop 22 is a board on which the subject P is placed.

The gantry 10 performs helical scan for helically scanning the subject P by rotating the rotary frame 15 while moving the tabletop 22. Alternatively, the gantry 10 performs conventional scan for scanning the subject P along the circular path by rotating the rotary frame 15, with the position of the subject P being fixed after moving the tabletop 22. Alternatively, the gantry 10 performs a step-and-shoot method that performs the conventional scan in a plurality of scan areas by moving the position of the tabletop 22 at a regular interval.

The console 30 is an apparatus that receives an operation of the X-ray CT apparatus 5 by an operator, and reconfigures the X-ray CT image data by using the projection data acquired by the gantry 10. The console 30 includes, as illustrated in FIG. 2, an input interface 31, a display 32, the scan control circuitry 33, the pre-processing circuitry 34, a memory 35, image reconfiguration circuitry 36, and processing circuitry 37.

The input interface 31 includes a mouse, a keyboard, a track ball, a switch, a button, a joystick, and the like to be used for input of various instructions and various settings by the operator of the X-ray CT apparatus 5, and transfers pieces of information of instructions and settings received from the operator to the processing circuitry 37. For example, the input interface 31 receives imaging conditions of X-ray CT image data, reconfiguration conditions at the time of reconfiguring the X-ray CT image data, and image processing conditions with respect to the X-ray CT image data from the operator. Further, the input interface 31 receives an operation for selecting an examination with respect to the subject P. The input interface 31 also receives a designation operation for designating a portion on the image.

The display 32 is a monitor referred to by the operator, and displays image data generated from the X-ray CT image data, and displays a GUI (Graphical User Interface) for receiving various instructions and various settings from the operator via the input interface 31, under control of the processing circuitry 37. Further, the display 32 displays, for example, a schedule screen for a scan schedule and a screen during scanning. Further, the display 32 displays, for example, exposure information and image data.

The scan control circuitry 33 controls the operations of the X-ray radiation control circuitry 11, the gantry drive circuitry 16, the data acquisition circuitry 14, and the bed drive device 21 under control of the processing circuitry 37, to control acquisition processing of the projection data on the gantry 10. Specifically, the scan control circuitry 33 respectively controls the acquisition processing of the projection data in imaging for acquiring a positioning image (a scanogram image) and in main imaging (scan) for acquiring an image to be used for diagnosis. In the X-ray CT apparatus 5 according to the first embodiment, two-dimensional scanogram images and three-dimensional scanogram images can be taken.

For example, the scan control circuitry 33 takes a two-dimensional scanogram image by fixing the X-ray tube 12a at a position of 0 degree (a position in a front direction with respect to the subject P) and continuously taking images while moving the tabletop 22 at a constant speed. Alternatively, the scan control circuitry 33 takes a two-dimensional scanogram image by fixing the X-ray tube 12a at the position of 0 degree and intermittently taking images synchronously with the movement of the tabletop, while moving the tabletop 22 intermittently. The scan control circuitry 33 can take the positioning image not only from the front direction with respect to the subject P, but also from an arbitrary direction (for example, from the side).

Further, the scan control circuitry 33 takes three-dimensional scanogram images by acquiring pieces of projection data for the entire perimeter of the subject P at the time of taking the scanogram image. For example, the scan control circuitry 33 acquires pieces of projection data for the entire perimeter of the subject P by performing helical scan or non-helical scan. Here, the scan control circuitry 33 performs helical scan or non-helical scan with a lower radiation dose than that of the main imaging, with respect to a wide range such as the entire breast region, entire abdominal region, entire upper body, entire body, and the like. As the non-helical scan, for example, the step-and-shoot scan described above is performed.

In this manner, since the scan control circuitry 33 acquires the pieces of projection data for the entire perimeter of the subject P, the image reconfiguration circuitry 36 described later can reconfigure the three-dimensional X-ray CT image data (volume data), and can generate a positioning image from an arbitrary direction by using the reconfigured volume data. Here, it can be set arbitrarily by the operator or can be preset according to examination contents whether to take a two-dimensional positioning image or a three-dimensional positioning image.

The pre-processing circuitry 34 generates corrected projection data by performing logarithmic conversion processing and correction processing such as offset correction, sensitivity correction, and beam hardening correction with respect to the projection data generated by the data acquisition circuitry 14. Specifically, the pre-processing circuitry 34 generates corrected projection data with regard to each of the pieces of projection data of the positioning image generated by the data acquisition circuitry 14 and projection data acquired by the main imaging, and stores these pieces of corrected projection data in the memory 35.

The memory 35 memorizes therein the projection data generated by the pre-processing circuitry 34. Specifically, the memory 35 memorizes therein the projection data of the positioning image generated by the pre-processing circuitry 34 and the projection data for diagnosis acquired by the main imaging. Further, the memory 35 memorizes therein the image data generated by the image reconfiguration circuitry 36 described later. The memory 35 also memorizes therein processing results acquired by the processing circuitry 37 described later appropriately. The processing results acquired by the processing circuitry 37 are described later.

The image reconfiguration circuitry 36 reconfigures the X-ray CT image data by using the projection data memorized in the memory 35. Specifically, the image reconfiguration circuitry 36 reconfigures the pieces of X-ray CT image data respectively from the projection data of the positioning image and the projection data of an image used for diagnosis. Here, as the reconfiguration method, there are various methods, and for example, back projection processing can be cited. Further, as the back projection processing, for example, back projection processing by using an FBP (Filtered Back Projection) method can be cited. Alternatively, the image reconfiguration circuitry 36 can reconfigure the X-ray CT image data by using successive approximation.

Further, the image reconfiguration circuitry 36 generates image data by performing various types of image processing with respect to the X-ray CT image data. The image reconfiguration circuitry 36 stores the reconfigured X-ray CT image data and image data generated by performing the various types of image processing in the memory 35.

The processing circuitry 37 controls operations of the gantry 10, the bed 20, and the console 30, to execute overall control of the X-ray CT apparatus 5. Specifically, the processing circuitry 37 controls CT scan performed by the gantry 10 by controlling the scan control circuitry 33. The processing circuitry 37 also controls the image reconfiguration processing and image generation processing in the console 30 by controlling the image reconfiguration circuitry 36. Further, the processing circuitry 37 executes control so that the various types of image data memorized in the memory 35 are displayed on the display 32.

Further, the processing circuitry 37 performs an acquisition function 37a and a control function 37b as illustrated in FIG. 2. Here, the respective processing functions performed by the acquisition function 37a and the control function 37b, which are constituent elements of the processing circuitry 37, for example, illustrated in FIG. 2 are recorded in the memory 35 in a form of programs executable by a computer. The processing circuitry 37 is a processor that reads the respective programs from the memory 35 and executes the programs to realize the functions corresponding to the respective programs. In other words, the processing circuitry 37 in a state having read the respective programs has the respective functions indicated in the processing circuitry 37 in FIG. 2. The acquisition function 37a is also referred to as "acquisition unit", and the control function 37b is also referred to as "control unit".

The configuration of the X-ray CT apparatus 5 according to the first embodiment has been described above. With this configuration, the X-ray CT apparatus 5 according to the first embodiment performs imaging of a subject, following imaging thereof by a PET apparatus.

In a general medical image diagnostic system, respective medical image diagnostic apparatuses may have a function of managing radiation dose information such as effective dose, absorbed dose, and exposed dose. Further, a general X-ray CT apparatus may have a function of displaying a warning text when an imaging condition exceeding a certain radiation dose is selected before exposure, a function of limiting exposure by a person having no authority by making the person input a password, and the like.

However, in the general medical image diagnostic system, the amount of radiation exposure by a plurality of medical image diagnostic apparatuses cannot be managed. For example, when imaging is performed by a general medical image diagnostic apparatus following imaging by another medical image diagnostic apparatus, the general medical image diagnostic apparatus does not have a function of confirming imaging conditions thereof, displaying a warning, or limiting the exposure based on radiation dose information at the time of imaging by the other medical image diagnostic apparatus. More specifically, the X-ray CT apparatus 5 does not have a function of confirming the imaging conditions, displaying a warning text, or limiting the exposure based on the radiation dose information at the time of imaging by the PET apparatus. Therefore, as for the medical image diagnostic system 1 according to the first embodiment, a case where the X-ray CT apparatus 5 performs a radiation dose management function described below to confirm the imaging conditions, display a warning, or limit the exposure based on the radiation dose information at the time of imaging by the PET apparatus is described. The radiation dose management function is realized by performing the acquisition function 37a and the control function 37b by the processing circuitry 37.

Figure 3:
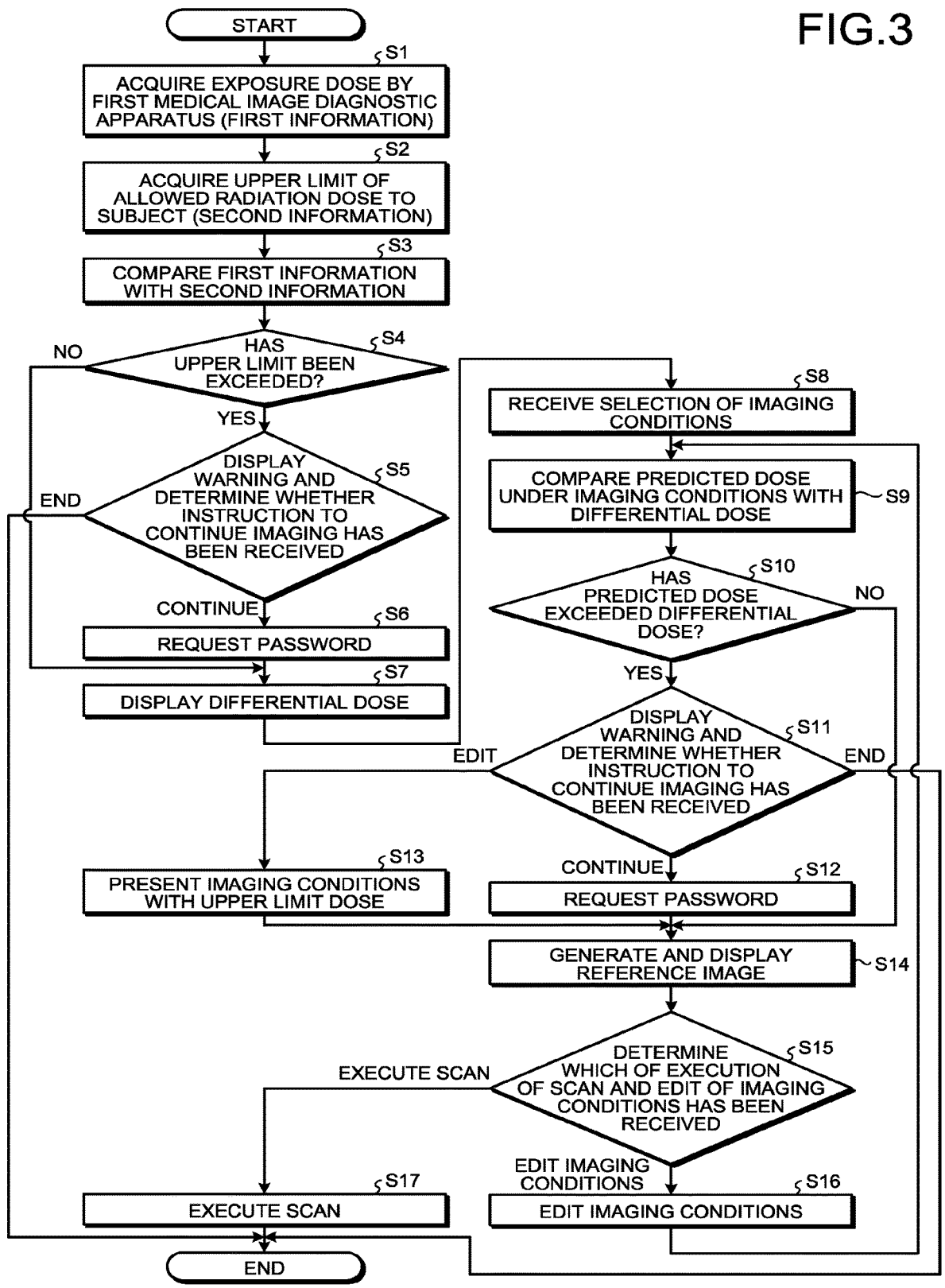
FIG. 3 is a flowchart illustrating a process procedure performed by processing circuitry according to the first embodiment.

The radiation dose management function by the processing circuitry 37 according to the first embodiment is described below with reference to FIG. 3 to FIG. 10. FIG. 3 is a flowchart illustrating a process procedure performed by the processing circuitry 37 according to the first embodiment. FIG. 4 to FIG. 10 are explanatory diagrams of the first embodiment.

FIG. 3 illustrates a flowchart for explaining an operation of the processing circuitry 37 and explains to which step in the flowchart each constituent element corresponds. From Step S1 to Step S2 are steps corresponding to the acquisition function 37a, at which the processing circuitry 37 realizes the acquisition function 37a by invoking a predetermined program corresponding to the acquisition function 37a from the memory 35 to execute the program. At Step S1, the acquisition function 37a acquires an exposure dose (first information) by the first medical image diagnostic apparatus 2. In other words, the acquisition function 37a acquires the first information related to the exposure dose of a subject by first imaging of the subject performed by the first medical image diagnostic apparatus 2 related to radiation. For example, when the first medical image diagnostic apparatus 2 is a PET apparatus, the acquisition function 37a acquires the type of radioactive agent and an injection amount, which are the imaging conditions, and calculates an absorbed dose of the subject from the acquired imaging conditions.

Subsequently, the acquisition function 37a acquires second information related to a reference dose. For example, the acquisition function 37a acquires an upper limit of an allowed radiation dose to the subject as the second information, as illustrated at Step S2 in FIG. 3. For example, the acquisition function 37a acquires the upper limit memorized in the memory 35. The upper limit here can be a radiation dose legally prescribed in each country or a value recommended by an academic society related to the department of radiology in each country, for example, a diagnostic reference level set by the J-RIME (Japan Network for Research and Information on Medical Exposure) or a radiation dose defined in hospitals. Further, the acquisition function 37a can receive an input of the upper limit from an operator.

Step S3 to Step S16 are steps corresponding to the control function 37b, at which the processing circuitry 37 realizes the control function 37b by invoking a predetermined program corresponding to the control function 37b from the memory 35 to execute the program. At Step S3 to Step S16, the control function 37b derives third information related to second imaging based on the second information related to the allowed radiation dose to the subject and the first information, before starting the second imaging of the subject performed after the first imaging by the second medical image diagnostic apparatus 3 related to radiation, and executes control to output the third information to the display 32. The third information is also referred to as "reference information".

For example, at Step S3, the control function 37b compares the first information acquired at Step S1 with the second information acquired at Step S2. In other words, the control function 37b compares the exposure dose indicated by the first information acquired at Step S1 with the upper limit indicated by the second information acquired at Step S2.

At Step S4, the control function 37b determines whether the upper limit has been exceeded. In other words, the control function 37b determines whether the exposure dose indicated by the first information acquired at Step S1 has exceeded the upper limit indicated by the second information acquired at Step S2. When determining that the exposure dose has not exceeded the upper limit (NO at Step S4), the control function 37b proceeds to Step S7. On the other hand, when determining that the exposure dose has exceeded the upper limit (YES at Step S4), the control function 37b displays a warning, and determines whether an instruction to continue imaging has been received (Step S5). That is, when the exposure dose indicated by the first information has exceeded the allowed radiation dose indicated by the second information, the control function 37b generates warning information indicating that the radiation dose exceeds the allowed radiation dose to the subject as the third information, before accepting the imaging conditions of the second imaging.

Figure 4:
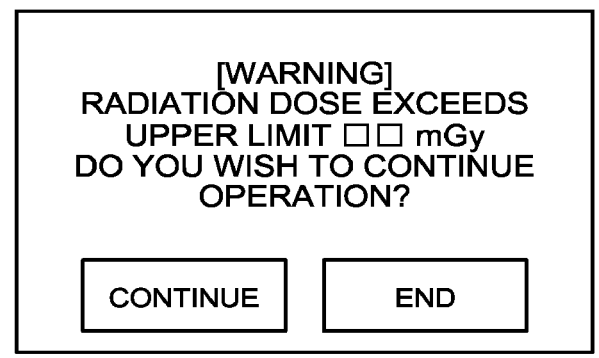
FIG. 4 is an explanatory diagram of the first embodiment.

For example, the control function 37b generates warning information including "[WARNING] RADIATION DOSE EXCEEDS UPPER LIMIT" as the third information as illustrated in FIG. 4. Further, the control function 37b generates warning information including "DO YOU WISH TO CONTINUE OPERATION? CONTINUE, END" as the third information. Here, when it is determined that an instruction to continue imaging is not received (END at Step S5), the control function 37b ends the processing. For example, when having received an operation to select "END" indicated in FIG. 4 from an operator, the control function 37b determines that selection to continue the operation has not been received, and ends the processing.

Figure 5:
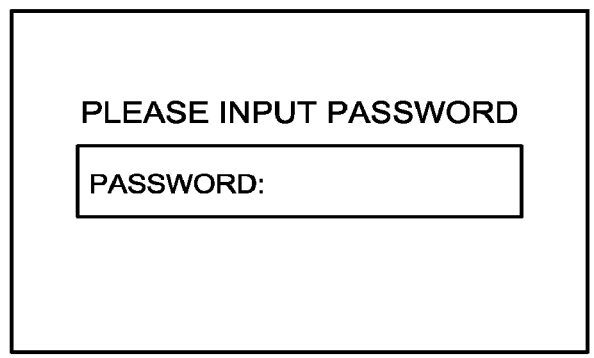
FIG. 5 is an explanatory diagram of the first embodiment.

Further, when it is determined that an instruction to continue imaging has been received (CONTINUE at Step S5), the control function 37b proceeds to Step S6. For example, when having received an operation to select "CONTINUE" indicated in FIG. 4 from the operator, the control function 37b determines that selection to continue the operation has been received, and requests a password (Step S6). In other words, when the exposure dose indicated by the first information has exceeded the allowed radiation dose indicated by the second information, the control function 37b generates request information for requesting reception of an operator's approval as the third information. For example, the control function 37b generates request information including "PLEASE INPUT PASSWORD" and "PASSWORD:" as a password input column as illustrated in FIG. 5 as the third information.

At Step S7, the control function 37b displays a differential dose. In other words, the control function 37b generates information indicating a differential dose between the allowed radiation dose indicated by the second information and the exposure dose indicated by the first information as the third information. For example, the control function 37b generates the third information including information indicating "RADIATION DOSE UP TO UPPER LIMIT IS oo mGy" as the differential dose as illustrated in FIG. 6.

Figure 6:
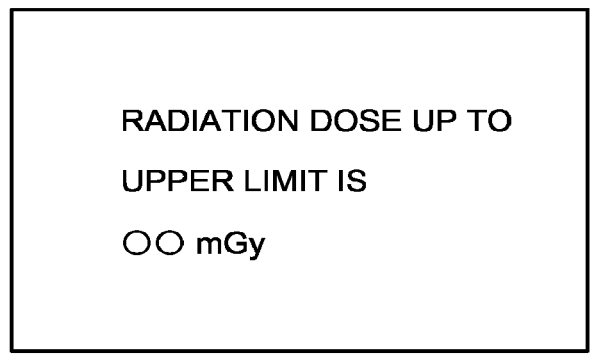
FIG. 6 is an explanatory diagram of the first embodiment.

A sentence "DOSE UP TO UPPER LIMIT IS oo mGy" is illustrated as the information indicating the differential dose in FIG. 6; however, the first embodiment is not limited thereto. For example, the control function 37b can display a graph or a numerical value as the information indicating the differential dose. As an example, the control function 37b can indicate the differential dose by displaying the exposure dose indicated by the first information in a graph, and displaying the allowed radiation dose indicated by the second information on the graph.

At Step S8, the control function 37b receives selection of the imaging conditions. For example, the control function 37b receives designation of an imaging portion, an imaging range, a tube voltage, a tube current, helical pitch, and the like from the operator. At Step S9, the control function 37b compares a predicted dose under the imaging conditions with the differential dose. The control function 37b obtains an exposure dose if scan is performed under the imaging conditions as the predicted dose based on the imaging conditions received at Step S8.

At Step S10, the control function 37b determines whether the predicted dose has exceeded the differential dose in a comparison result at Step S9. In other words, the control function 37b determines whether the predicted dose based on the imaging conditions received at Step S8 has exceeded the differential dose displayed at Step S7. When determining that the predicted dose has not exceeded the differential dose (NO at Step S10), the control function 37b proceeds to Step S14. On the other hand, when determining that the predicted dose has exceeded the differential dose (YES at Step S10), the control function 37b displays a warning and determines whether an instruction to continue imaging has been received (Step S11). That is, when the total dose of the exposure dose indicated by the first information and the exposure dose of the subject by the second imaging that is estimated from the imaging conditions of the second imaging has exceeded the allowed radiation dose indicated by the second information, the control function 37b generates warning information indicating that the total dose exceeds the allowed radiation dose to the subject as the third information.

Figure 7:
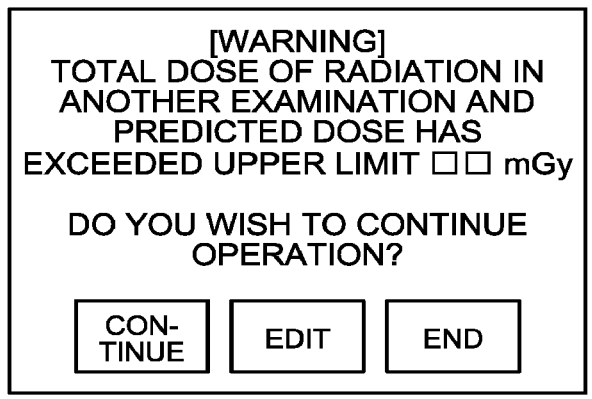
FIG. 7 is an explanatory diagram of the first embodiment.

For example, the control function 37b generates warning information including "[WARNING] TOTAL DOSE OF RADIATION IN ANOTHER EXAMINATION AND PREDICTED DOSE HAS EXCEEDED UPPER LIMIT □□ mGy" as the third information, as illustrated in FIG. 7. Further, the control function 37b generates warning information including "IS IMAGING TO BE CONTINUED? CONTINUE, EDIT, END" as the third information. When not determining that an instruction to continue imaging has been received (END at Step S11), the control function 37b ends the processing. For example, when having received an operation to select "END" illustrated in FIG. 7 from the operator, the control function 37b determines that the selection to continue the operation has not been received and ends the processing.

In FIG. 4 to FIG. 7, the unit of the total dose of the radiation dose in another examination and the predicted dose is described as "Gy"; however, the first embodiment is not limited thereto. For example, the control function 37b can calculate the total dose of the radiation dose in another examination and the predicted dose by "Sv". That is, when the exposure dose by a radioactive agent and the exposure dose by X-ray exposure are added, it is necessary to justify the unit. The unit to be used can be selected arbitrarily.

Further, in FIG. 7, a case where the sentence indicating "[WARNING] TOTAL DOSE OF RADIATION IN ANOTHER EXAMINATION AND PREDICTED DOSE HAS EXCEEDED UPPER LIMIT □□ mGy" is displayed has been described; however, the first embodiment is not limited thereto. For example, the control function 37b can display the total dose of the radiation dose in another examination and the predicted dose, and the upper limit in a graph or a numerical value. As an example, the control function 37b can indicate the differential dose by displaying the total dose of the radiation dose in another examination and the predicted dose in a graph and displaying the upper limit on the graph.

Figure 8:
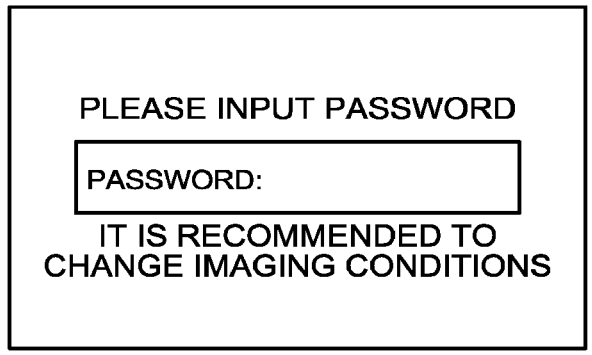
FIG. 8 is an explanatory diagram of the first embodiment.

Further, when having received an operation to select "CONTINUE" illustrated in FIG. 7 from the operator (CONTINUE at Step S11), the control function 37b determines that selection to continue imaging under the imaging conditions selected at Step S8 has been received, and requests a password (Step S12). In other words, when the total dose of the exposure dose indicated by the first information and the exposure dose of the subject by the second imaging estimated from the imaging conditions of the second imaging has exceeded the allowed radiation dose indicated by the second information, the control function 37b generates request information for requesting reception of the operator's approval as the third information. For example, the control function 37b generates request information including "PLEASE INPUT PASSWORD" and "PASSWORD:" as a password input column as illustrated in FIG. 8 as the third information. The control function 37b can generate recommendation information suggesting a change of the exposure conditions as the third information. For example, the control function 37b generates the third information including "IT IS RECOMMENDED TO CHANGE IMAGING CONDITIONS" as illustrated in FIG. 8. That is, when the total dose of the exposure dose indicated by the first information and the exposure dose of the subject by the second imaging estimated from the imaging conditions of the second imaging has exceeded the allowed radiation dose indicated by the second information, the control function 37b generates recommendation information suggesting a change of the set imaging conditions of the second imaging as the third information.

Further, when having received an operation to select "EDIT" illustrated in FIG. 7 from the operator (EDIT at Step S11), the control function 37b determines that selection to edit the imaging conditions to the upper limit dose and continue imaging has been received, and presents the imaging conditions with the upper limit dose (Step S13).

Figure 9:
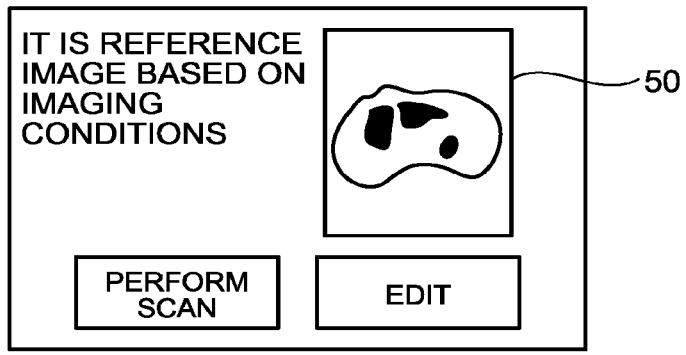
FIG. 9 is an explanatory diagram of the first embodiment.

After end of Step S12 or after end of Step S13, the control function 37b generates and displays a reference image at Step S14. In other words, the control function 37b outputs a reference image predicting an image acquired by the set imaging conditions of the second imaging as the third information. For example, the control function 37b generates a reference image 50 as the third information, as illustrated in FIG. 9, and displays the reference image 50 on the display 32. The control function 37b can generate the third information including "IT IS REFERENCE IMAGE BASED ON IMAGING CONDITIONS" and display the third information together with the reference image 50 on the display 32.

At Step S15, the control function 37b determines which of execution of scan or edit of imaging conditions has been received. For example, when having received an operation to select "EXECUTE SCAN" illustrated in FIG. 9 from the operator, the control function 37b determines that execution of scan has been received. When having received an operation to select "EDIT" illustrated in FIG. 9 from the operator, the control function 37b determines that edit of imaging conditions has been received. When determining that execution of scan has been received (YES at Step S15), the control function 37b proceeds to Step S17. On the other hand, when not determining that execution of scan has been received (NO at Step S15), the control function 37b proceeds to Step S16.

Figure 10:
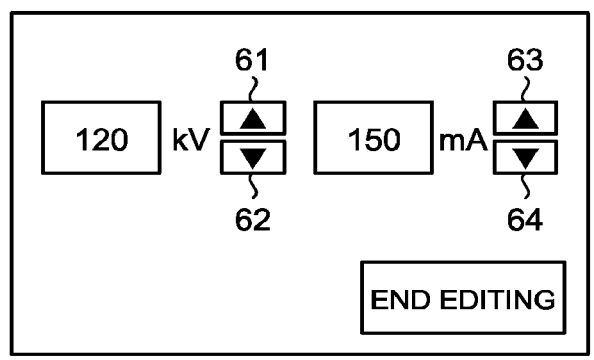
FIG. 10 is an explanatory diagram of the first embodiment.

At Step S16, the control function 37b receives edit of the imaging conditions. For example, as illustrated in FIG. 10, the control function 37b displays a GUI for inputting a parameter related to image quality on the display 32. In an example in FIG. 10, a case where the control function 37b receives at least one change of the tube voltage and the tube current as the parameter related to image quality is illustrated. More specifically, in the example illustrated in FIG. 10, the tube voltage is set to 120 kV and the tube current is set to 150 mA. Here, the operator changes the tube voltage by operating an increase button 61 or a decrease button 62 and changes the tube current by operating an increase button 63 or a decrease button 64 via the input interface 31. In other words, the operator inputs a parameter related to image quality via the input interface 31. The control function 37b receives selection of "END EDITING" illustrated in FIG. 10 from the operator, to complete the processing to edit the imaging conditions. Thus, the control function 37b edits the imaging conditions of the second imaging based on the parameter related to image quality input via the input interface 31. After end of Step S17, the control function 37b proceeds to Step S9.

Step S17 is a step realized by the processing circuitry 37. At Step S17, the processing circuitry 37 performs scan by controlling the scan control circuitry 33. For example, upon reception of a change of the imaging conditions, the processing circuitry 37 controls the scan control circuitry 33 so as to execute scan under the imaging conditions received at Step S16. On the other hand, when a change of the imaging conditions has not been received, the processing circuitry 37 controls the scan control circuitry 33 so as to execute scan under the imaging conditions received at Step S8.

As described above, according to the first embodiment, the second medical image diagnostic apparatus 3 related to radiation derives the third information related to the second imaging, based on the second information related to the allowed radiation dose to the subject and the first information related to the exposure dose of the subject by the first imaging, before starting the second imaging of the subject to be performed after the first imaging performed on the subject by the first medical image diagnostic apparatus 2 related to radiation. Consequently, according to the first embodiment, the exposure dose by a plurality of medical image diagnostic apparatuses can be managed.

According to the first embodiment, when the total dose of the exposure dose indicated by the first information and the exposure dose of the subject by the second imaging that is estimated from the imaging conditions of the second imaging has exceeded the allowed radiation dose indicated by the second information, the third information is generated. Consequently, according to the first embodiment, when imaging of a subject is performed exceeding an allowed radiation dose, it can be requested to receive an operator's approval and it can be recommended to change the imaging conditions.

According to the first embodiment, the reference image predicting an image acquired by the set imaging conditions of the second imaging is output as the third information. Consequently, the operator can set the imaging conditions that can be used for image diagnosis in which the exposure dose is suppressed to the minimum by confirming the reference image.

In the first embodiment described above, a case where imaging is performed by the X-ray CT apparatus 5 after imaging by the PET apparatus has been described; however, the present embodiment is not limited thereto. For example, the PET apparatus can perform imaging after imaging by the X-ray CT apparatus 5.

In this case, the PET apparatus acquires the exposure dose by imaging performed by the X-ray CT apparatus 5, and compares the exposure dose with the upper limit to generate the third information. Further, the PET apparatus receives the type and an injection dose of a radioactive agent to be injected, and a residence time of the radioactive agent from the operator as the imaging conditions. Subsequently, the PET apparatus predicts the exposure dose under the received imaging conditions, and calculates the total dose of the predicted dose and the exposure dose by imaging performed by the X-ray CT apparatus 5. The PET apparatus compares the calculated total dose with the upper limit to generate the third information. The PET apparatus described in the first embodiment described above can be replaced by a SPECT apparatus.

In the first embodiment described above, a case where the medical image diagnostic system 1 includes the PET apparatus and the X-ray CT apparatus 5 has been described. The medical image diagnostic system 1 may include an X-ray CT apparatus and an X-ray diagnostic apparatus. In such a medical image diagnostic system 1, an intervention treatment using the X-ray CT apparatus and the X-ray diagnostic apparatus may be performed. In the intervention treatment, imaging by the X-ray CT apparatus is performed following imaging by the X-ray diagnostic apparatus, and thereafter, imaging by the X-ray diagnostic apparatus may be performed again.

Also in the intervention treatment using the X-ray CT apparatus and the X-ray diagnostic apparatus together, the exposure dose can be managed integrally. Therefore, in a second embodiment, a case where after imaging by the X-ray CT apparatus is performed following imaging by the X-ray diagnostic apparatus, imaging by the X-ray diagnostic apparatus is performed again is described. The configuration example of the X-ray CT apparatus 5 according to the second embodiment is identical to that of the X-ray CT apparatus 5 according to the first embodiment illustrated in FIG. 2, and therefore detailed explanations thereof are omitted.

Figure 11:
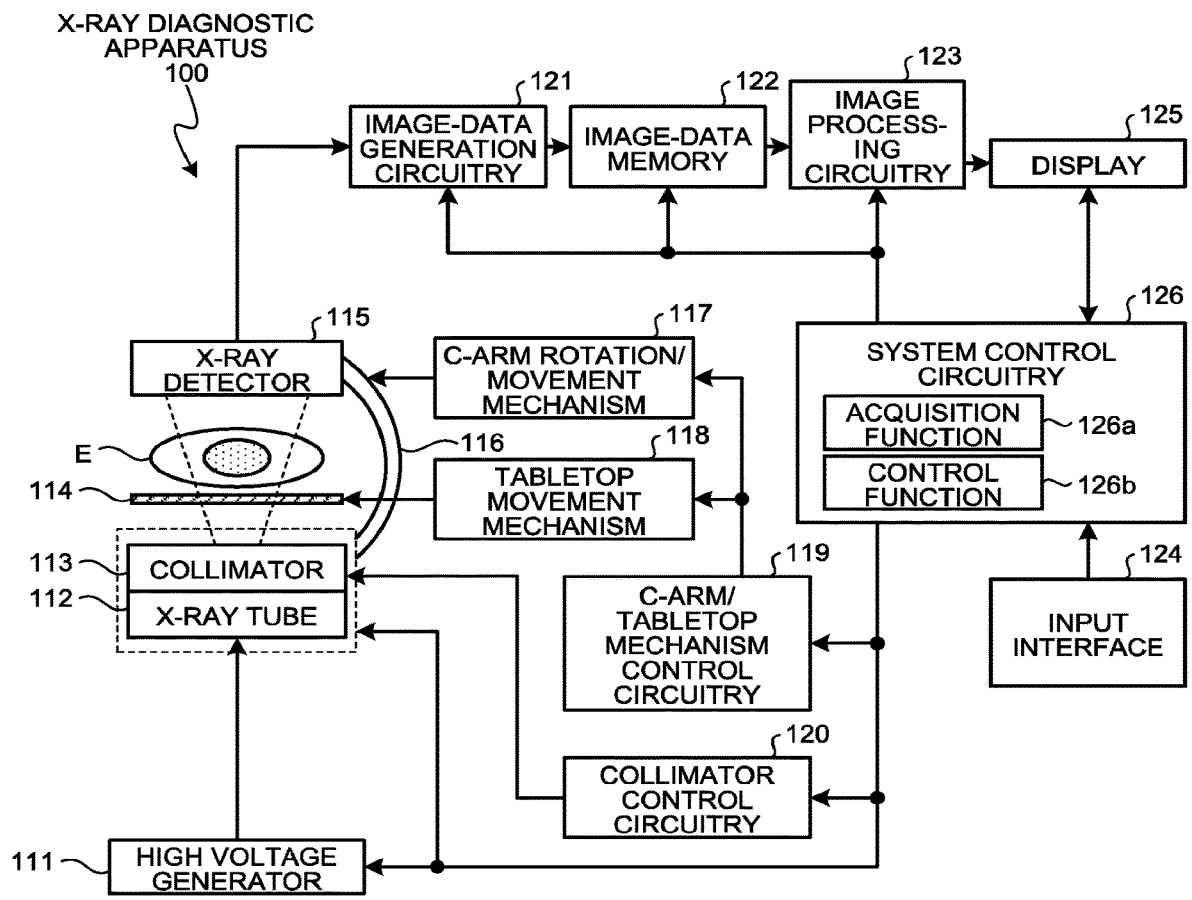
FIG. 11 is a block diagram illustrating a configuration example of an X-ray diagnostic apparatus according to a second embodiment.

FIG. 11 is a block diagram illustrating a configuration example of an X-ray diagnostic apparatus 100 according to the second embodiment. As illustrated in FIG. 11, the X-ray diagnostic apparatus 100 according to the second embodiment includes a high voltage generator 111, an X-ray tube 112, a collimator 113, a tabletop 114, an X-ray detector 115, a C-arm 116, a C-arm rotation/movement mechanism 117, a tabletop movement mechanism 118, C-arm/tabletop mechanism control circuitry 119, collimator control circuitry 120, image-data generation circuitry 121, an image-data memory 122, image processing circuitry 123, an input interface 124, a display 125, and system control circuitry 126.

The high voltage generator 111 is a device that generates a high voltage, and supplies the generated high voltage to the X-ray tube 112. The X-ray tube 112 is an X-ray source that generates X rays by using the high voltage supplied from the high voltage generator 111. The high voltage generator 111 performs adjustment of X-ray dosage applied to a subject E and executes control of ON/OFF of X-ray radiation to the subject E by adjusting the voltage supplied to the X-ray tube 112.

The collimator 113 is a device that narrows down X rays generated by the X-ray tube 112 so as to selectively irradiate the X rays to a region of interest of the subject E. For example, the collimator 113 has four slidable diaphragm blades, and narrows down X rays generated by the X-ray tube 112 by sliding these diaphragm blades and irradiates the subject E with narrowed X rays.

The tabletop 114 is a bed on which the subject E is placed, and is arranged on a bed (not illustrated).

The X-ray detector 115 is a device in which a plurality of X-ray detection elements are arranged in a matrix in order to detect X rays having transmitted through the subject E. The respective X-ray detection elements provided in the X-ray detector 115 convert the X rays having transmitted through the subject E to electric signals and accumulate the electric signals, and transmit the accumulated electric signals to the image-data generation circuitry 121 described later.

The C-arm 116 is a C-shaped arm that holds the X-ray tube 112, the collimator 113, and the X-ray detector 115. The C-arm 116 holds the X-ray tube 112 and the collimator 113, and the X-ray detector 115 so that the X-ray tube 112 and the collimator 113, and the X-ray detector 115 face each other with the subject E placed therebetween. A mechanism configured by the C-arm 116, the X-ray tube 112, the collimator 113, and the X-ray detector 115 is referred to as "imaging unit". In the following descriptions, it is assumed that the X-ray diagnostic apparatus 100 is a single-plane X-ray diagnostic apparatus having one C-arm 116.

The C-arm rotation/movement mechanism 117 is a device that rotates and moves the C-arm 116. The C-arm rotation/movement mechanism 117 rotates the C-arm 116 around a rotation shaft that passes between the X-ray tube 112 and the X-ray detector 115.

The tabletop movement mechanism 118 is a device that moves the tabletop 114. The C-arm/tabletop mechanism control circuitry 119 is a processing unit that performs rotation adjustment and movement adjustment of the C-arm 116 and movement adjustment of the tabletop 114 by controlling the C-arm rotation/movement mechanism 117 and the tabletop movement mechanism 118.

The collimator control circuitry 120 is a processing unit that controls an X-ray radiation range by adjusting an aperture of the diaphragm blades provided in the collimator 113.

The image-data generation circuitry 121 is a processing unit that generates X-ray image data by using the electric signals converted from X rays having transmitted through the subject E by the X-ray detector 115, and stores the generated X-ray image data in the image-data memory 122. Specifically, the image-data generation circuitry 121 generates the X-ray image data by performing current/voltage conversion, A/D conversion, and parallel/serial conversion with respect to the electric signals received from the X-ray detector 115. For example, the image-data generation circuitry 121 is an integrated circuit such as an ASIC (Application Specific Integrated Circuit) and an FPGA (Field Programmable Gate Array), or an electronic circuit such as a CPU (Central Processing Unit) and an MPU (Micro Processing Unit).

The image-data memory 122 is a memory device that memorizes therein the X-ray image data generated by the image-data generation circuitry 121. Further, the image-data memory 122 may memorize therein X-ray image data image-processed by the image processing circuitry 123. For example, the image-data memory 122 is a semiconductor memory device such as a RAM (Random Access Memory) and a flash memory, or a hard disk, an optical disk, and the like.

The image processing circuitry 123 is a processing unit that performs various types of image processing with respect to the X-ray image data memorized in the image-data memory 122. For example, the image processing circuitry 123 performs recursive filter processing (time filter processing) and isotropic diffusion filter processing (space filter processing) for noise reduction with respect to the X-ray image data. For example, the image processing circuitry 123 is an integrated circuit such as an ASIC and an FPGA, or an electronic circuit such as a CPU and an MPU.

The input interface 124 is an input device that receives various commands from an operator such as a doctor or a radiation technologist who operates the X-ray diagnostic apparatus 100, and transfers the received commands to the system control circuitry 126. For example, the input interface 124 includes a mouse, a keyboard, a button, a track ball, a joystick, and the like for receiving various commands from an operator.

The display 125 is a display device that displays thereon a GUI (Graphical User Interface) for receiving commands from an operator via the input interface 124, X-ray image data memorized in the image-data memory 122, X-ray image data image-processed by the image processing circuitry 123, and the like. The display 125 is, for example, a liquid crystal display or a CRT (Cathode-Ray Tube) display. The display 125 includes, for example, a real-time monitor to be used for displaying X-ray image data being imaged, and a monitor for comparison to be used for displaying X-ray image data imaged in the past.

The system control circuitry 126 is a processing unit that controls operations of the X-ray diagnostic apparatus 100 in its entirety. The system control circuitry 126 is, for example, an electronic circuit such as a CPU (Central Processing Unit) or an MPU (Micro Processing Unit). The system control circuitry 126 controls the high voltage generator 111, the C-arm/tabletop mechanism control circuitry 119, and the collimator control circuitry 120, for example, based on a command from the operator transferred from the input interface 124, to adjust the X-ray dosage, execute ON/OFF control of X-ray radiation, adjust rotation and movement of the C-arm 116, and adjust movement of the tabletop 114.

The system control circuitry 126 controls image generation processing in the image-data generation circuitry 121 and image processing in the image processing circuitry 123 described later based on a command from the operator. Moreover, the system control circuitry 126 executes control so that the GUI for receiving a command from the operator, X-ray image data memorized in the image-data memory 122, X-ray image data image-processed by the image processing circuitry 123, and the like are displayed on a monitor of the display 125.

The system control circuitry 126 performs an acquisition function 126a and a control function 126b as illustrated in FIG. 11. Here, for example, the respective processing functions performed by the acquisition function 126a and the control function 126b, which are constituent elements of the system control circuitry 126 illustrated in FIG. 11 are recorded in the image-data memory 122 in a form of programs executable by a computer. The system control circuitry 126 is a processor that reads the respective programs from the image-data memory 122 and executes the programs to realize the functions corresponding to the respective programs. In other words, the system control circuitry 126 in a state having read the respective programs has the respective functions illustrated in the system control circuitry 126 in FIG. 11. The acquisition function 126a is also referred to as "acquisition unit", and the control function 126b is also referred to as "control unit".

The overall configuration of the X-ray diagnostic apparatus 100 according to the second embodiment has been described above. With this configuration, the X-ray diagnostic apparatus 100 according to the second embodiment receives imaging conditions of first imaging. Here, for example, the X-ray diagnostic apparatus 100 receives, as the imaging conditions, settings of a tube current, a tube voltage, a radiation interval of X-ray pulses, and the like. The X-ray diagnostic apparatus 100 emits X-rays under the received imaging conditions. The X-ray diagnostic apparatus 100 calculates an exposure dose based on an X-ray radiation time at the time of imaging and the received imaging conditions, and memorizes the calculated exposure dose in the image-data memory 122 as first information.

Subsequently, the X-ray CT apparatus 5 according to the second embodiment performs second imaging of the subject, following the first imaging by the X-ray diagnostic apparatus 100. The X-ray CT apparatus 5 according to the second embodiment performs a radiation dose management function in the same manner as described in the first embodiment. For example, the acquisition function 126a of the X-ray CT apparatus 5 performs the same function as the acquisition function 37a described in the first embodiment. For example, the acquisition function 126a acquires the first information being an exposure dose by imaging performed by the X-ray diagnostic apparatus 100 from the X-ray diagnostic apparatus 100.

Subsequently, the control function 126b of the X-ray CT apparatus 5 performs the same function as the control function 37b described in the first embodiment. For example, the control function 126b derives third information related to second imaging, based on second information related to the allowed radiation dose to the subject and the first information, before starting the second imaging with respect to the subject to be performed by the X-ray CT apparatus 5 after the first imaging by the X-ray diagnostic apparatus 100. The X-ray CT apparatus 5 executes control so that the derived third information is displayed on the display 32 of the X-ray CT apparatus 5.

The X-ray diagnostic apparatus 100 performs third imaging of the subject, following imaging by the X-ray CT apparatus 5. Here, the X-ray diagnostic apparatus 100 according to the second embodiment performs the same radiation dose management function as that of the first embodiment.

For example, the acquisition function 126a of the X-ray diagnostic apparatus 100 performs the same function as the acquisition function 37a described in the first embodiment. For example, the acquisition function 126a acquires the first information being an exposure dose by the second imaging performed by the X-ray CT apparatus 5. For example, the acquisition function 126a acquires imaging conditions of the second imaging set in the X-ray CT apparatus 5 as the first information. Further, when performing third imaging with respect to the subject, the acquisition function 126a acquires also an exposure dose by the first imaging as the first information from the image-data memory 122. In other words, the acquisition function 126a acquires a cumulative total value of the exposure dose up to start of imaging in the same examination, as the first information.

Subsequently, the control function 126b of the X-ray diagnostic apparatus 100 performs the same function as the control function 37b described in the first embodiment. For example, the control function 126b derives third information related to third imaging, based on the second information related to the allowed radiation dose to the subject, the first information acquired from the X-ray CT apparatus 5, and the first information acquired from the image-data memory 122, before start of imaging with respect to the subject performed in the X-ray diagnostic apparatus 100 after the imaging by the X-ray CT apparatus 5. The control function 126b executes control so that the derived third information is displayed on the display 125 of the X-ray diagnostic apparatus 100.

Further, the X-ray diagnostic apparatus 100 according to the second embodiment receives imaging conditions of the third imaging from the operator of the X-ray diagnostic apparatus 100 and emits X rays under the received imaging conditions. Here, the control function 126b receives settings of, for example, a radiation dose and a radiation interval of X-ray pulses as the imaging conditions. The control function 126b can further receive settings of an expected radiation time as the imaging conditions of the third imaging. Accordingly, the control function 126b can estimate an exposure dose in the third imaging to be performed next. The control function 126b then determines whether an upper limit is exceeded by adding the estimated exposure dose, the first information acquired from the X-ray CT apparatus 5, and the first information acquired from the image-data memory 122, to generate the third information. In other words, the control function 126b derives the third information related to the third imaging, based on the second information related to the allowed radiation dose to the subject, the first information acquired from the X-ray CT apparatus 5, the first information acquired from the image-data memory 122, and the estimated exposure dose. The control function 126b then executes control so that the derived third information is displayed on the display 125 of the X-ray diagnostic apparatus 100.

As described above, according to the second embodiment, after the second imaging by the X-ray CT apparatus 5 is performed following the first imaging by the X-ray diagnostic apparatus 100, when the third imaging by the X-ray diagnostic apparatus 100 is to be performed, the X-ray diagnostic apparatus 100 acquires the first information being the exposure dose by the second imaging performed by the X-ray CT apparatus 5, and the first information being the exposure dose by the first imaging. The X-ray diagnostic apparatus 100 then derives the third information related to the third imaging, based on the second information related to the allowed radiation dose to the subject, the first information related to the exposure dose of the subject by the first imaging, and the first information related to the exposure dose of the subject by the second imaging, before start of the third imaging. Consequently, according to the second embodiment, the amount of radiation exposure by a plurality of medical image diagnostic apparatuses can be managed.

According to the second embodiment, when a total dose of the exposure dose indicated by the first information and the exposure dose of the subject by the third imaging that is estimated from the imaging conditions of the third imaging exceeds the allowed radiation dose indicated by the second information, the third information is generated. Consequently, according to the second embodiment, when imaging of a subject is to be performed exceeding an allowed radiation dose, it can be requested to receive an operator's approval and it can be recommended to change the imaging conditions.

In imaging by the X-ray diagnostic apparatus 100, different from imaging by the X-ray CT apparatus 5, an end time varies depending on the skill of the operator, the shape of an area of the body to be treated, and the like. For example, if the operator can quickly perform the procedure without any trouble, imaging is completed within an estimated radiation time. However, if it takes time to insert a treatment device into the area of the body to be treated, imaging is not completed within the estimated radiation time. Thus, for example, when imaging is not completed within the estimated radiation time, the exposure dose of the subject increases, and the total dose of the exposure dose may exceed the upper limit.

Figure 12:
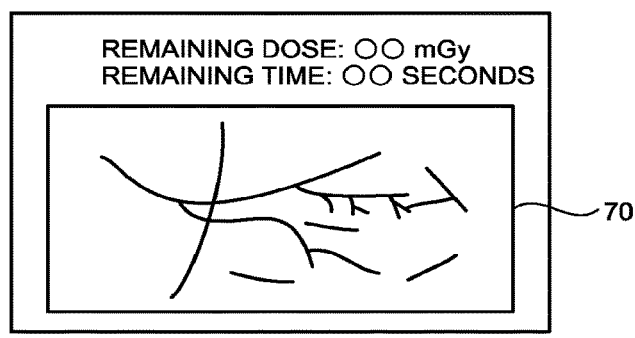
FIG. 12 is an explanatory diagram of a modification of the second embodiment.

Therefore, in a modification of the second embodiment, a case where an operator is notified of a temporal margin up to the upper limit and a margin of the exposure dose is described. A case where the first medical image diagnostic apparatus 2 is the X-ray CT apparatus 5, the second medical image diagnostic apparatus is the X-ray diagnostic apparatus 100, and second imaging by the X-ray diagnostic apparatus 100 is performed, following first imaging by the X-ray CT apparatus 5, in the medical image diagnostic system 1 is described below. In this case, the X-ray diagnostic apparatus 100 receives settings of imaging conditions and performs imaging, as in the second embodiment described above. FIG. 12 is an explanatory diagram of the modification of the second embodiment.

FIG. 12 illustrates the display 125 of the X-ray diagnostic apparatus 100. A fluoroscopic X-ray image 70 is displayed on the display 125. The control function 126b acquires the exposure dose by the second imaging on a real-time basis from the imaging conditions being applied in the second imaging. The control function 126b generates, on a real-time basis, information indicating at least one of a remaining exposable dose and a remaining exposable time based on the acquired radiation dose and a differential dose, as third information. The differential dose is a differential dose between the upper limit and the exposure dose by imaging by the X-ray CT apparatus 5. That is, the control function 126b generates a subtraction value by subtracting the exposure dose by imaging by the X-ray diagnostic apparatus 100 acquired on the real-time basis from the differential dose between the upper limit and the exposure dose by imaging by the X-ray CT apparatus 5, as the third information. Alternatively, the control function 126b calculates a time until reaching the upper limit based on the subtraction value and the imaging conditions, and generates the calculated time as the third information.

In the example illustrated in FIG. 12, the control function 126b generates the third information including "REMAINING DOSE: oo mGy" and "REMAINING TIME: oo SECONDS", and displays the generated third information on the display 125. Thus, in the modification of the second embodiment, the information indicating at least one of the remaining exposable dose and the remaining exposable time based on the acquired radiation dose and the differential dose as the third information on a real-time basis. Consequently, according to the modification of the second embodiment, in imaging by the X-ray diagnostic apparatus 100, an operator can ascertain the degree of progress of the procedure, and can pay attention so as to decrease exposure of the subject.

The embodiment is not limited to those described above.

Figure 13:
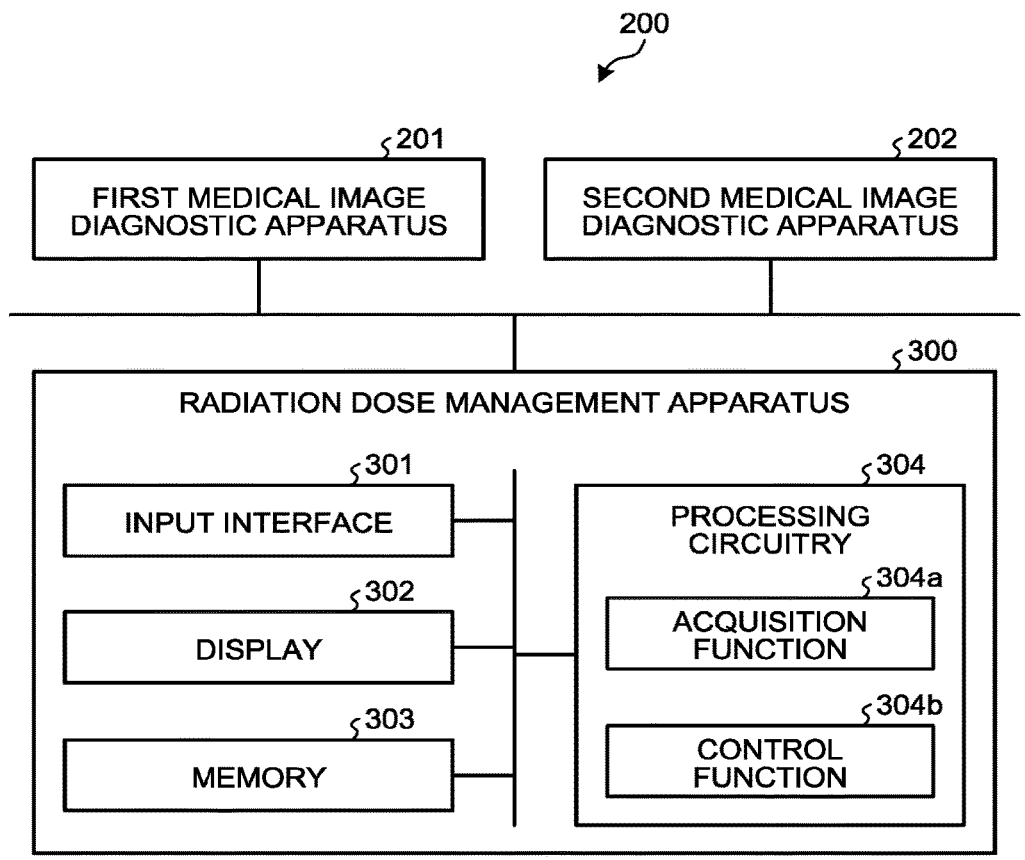
FIG. 13 is a block diagram illustrating a configuration example of a medical image diagnostic system according to another embodiment.

In the embodiments described above, a case where the radiation dose management function is performed in the second medical image diagnostic apparatus 3 has been described; however, the embodiments are not limited thereto. For example, the radiation dose management function can be performed by a third device provided in addition to the first medical image diagnostic apparatus 2 and the second medical image diagnostic apparatus 3. FIG. 13 is a block diagram illustrating a configuration example of a medical image diagnostic system 200 according to another embodiment.

As illustrated in FIG. 13, the medical image diagnostic system 200 according to the other embodiment includes a first medical image diagnostic apparatus 201 related to radiation, a second medical image diagnostic apparatus 202 related to radiation, and a radiation dose management apparatus 300. The first medical image diagnostic apparatus 201 is, for example, a PET apparatus, a SPECT apparatus, an X-ray CT apparatus, or an X-ray diagnostic apparatus, and the second medical image diagnostic apparatus 202 is, for example, a PET apparatus, a SPECT apparatus, an X-ray CT apparatus, or an X-ray diagnostic apparatus. In the medical image diagnostic system 200 according to the other embodiment, the first medical image diagnostic apparatus 201 and the second medical image diagnostic apparatus 202 may not have the radiation dose management function described in the first embodiment and the second embodiment, and may be set not to perform the radiation dose management function, although having the radiation dose management function.

Further, as illustrated in FIG. 13, the first medical image diagnostic apparatus 201 related to radiation, the second medical image diagnostic apparatus 202 related to radiation, and the radiation dose management apparatus 300 are connected to each other via a network. If connection is possible via the network, installation places of the first medical image diagnostic apparatus 201 related to radiation, the second medical image diagnostic apparatus 202 related to radiation, and the radiation dose management apparatus 300 are arbitrary. For example, the radiation dose management apparatus 300 can be installed in a hospital different from a hospital where the first medical image diagnostic apparatus 201 and the second medical image diagnostic apparatus 202 are installed. That is, the network in FIG. 13 can be configured by a local network closed within the hospital, or can be a network via the Internet.

The radiation dose management apparatus 300 includes an input interface 301, a display 302, a memory 303, and processing circuitry 304, and performs the radiation dose management function. The input interface 301 includes a mouse, a keyboard, a track ball, a switch, a button, a joystick, and the like to be used by an operator to input various instructions and various settings, and transfers information of the instructions and settings received from the operator to the processing circuitry 304.

The display 302 is a monitor referred to by an operator, and displays thereon a GUI for receiving various instructions and various settings from the operator via the input interface 301 under control of the processing circuitry 304.

The memory 303 memorizes therein various types of information. For example, the memory 303 memorizes therein first information being an exposure dose by imaging by the first medical image diagnostic apparatus 201 and second information being an upper limit of the exposure dose.

The processing circuitry 304 executes overall control of the radiation dose management apparatus 300. The processing circuitry 304 also performs an acquisition function 304a and a control function 304b, as illustrated in FIG. 13. Here, for example, the respective processing functions performed by the acquisition function 304a and the control function 304b, which are constituent elements of the processing circuitry 304 illustrated in FIG. 13, are recorded in the memory 303 in a form of programs executable by a computer. The processing circuitry 304 is a processor that reads respective programs from the memory 303 and executes the programs to realize the functions corresponding to the respective programs. In other words, the processing circuitry 304 in a state of having read the respective programs has the respective functions illustrated in the processing circuitry 304 in FIG. 13. The acquisition function 304a is also referred to as "acquisition unit", and the control function 304b is also referred to as "control unit".

In the medical image diagnostic system 200 configured in this manner, imaging by the second medical image diagnostic apparatus 202 is performed, following imaging by the first medical image diagnostic apparatus 201. In this case, the radiation dose management apparatus 300 performs the same radiation dose management function as that of the first embodiment and the second embodiment. For example, the acquisition function 304a performs the same function as the acquisition function 37a according to the first embodiment and the acquisition function 126a according to the second embodiment. Further, for example, the control function 304b performs the same function as the control function 37b according to the first embodiment and the control function 126b according to the second embodiment.

In the embodiments described above, a medical image diagnostic system including two medical image diagnostic apparatuses has been described; however, the embodiments are not limited thereto. The embodiments described above can be also applied to, for example, a medical image diagnostic system including three or more medical image diagnostic apparatuses.

In imaging by a PET apparatus and a SPECT apparatus, when an exposure dose is to be estimated, the exposure dose can be estimated, taking into consideration an internal organ in which a radioactive agent to be injected is easily accumulated. Further, the second information related to an allowed radiation dose to the subject can be set for each organ.

That is, the radioactive agent has a different accumulation degree in organs depending on the type thereof. On the other hand, an influence rate of exposure is different for each organ. Therefore, the accumulation degree for each organ is estimated, for example, based on the type of radioactive agent specified in the imaging conditions, and the influence rate for each organ corresponding to the type is acquired. Thereafter, by weighting the accumulation degree in respective organs by the influence rate of a concerned organ, detailed exposure dose for each organ in imaging by the PET apparatus and a SPECT apparatus can be predicted. The detailed exposure dose for each organ can be predicted, for example, by estimating the exposure dose for each organ based on the injection amount of the radioactive agent specified in the imaging conditions and the accumulation degree for each organ, and weighting the exposure dose by the influence rate. Further, by adding the accumulation degree weighted for each organ, an accurate whole-body exposure dose in imaging by the PET apparatus and a SPECT apparatus can be estimated. Accordingly, when the first medical image diagnostic apparatus 2 is a PET apparatus, highly accurate first information can be acquired. When the second medical image diagnostic apparatus 3 is a PET apparatus, the exposure dose of the subject by second imaging can be accurately estimated.

Here, the accumulation degree for each organ described above can be acquired, for example, by an agent standard distribution map prepared for each radioactive agent. When such a map is prepared, the first information related to the exposure dose of the subject by first imaging performed by the PET apparatus can be acquired from a PET image acquired by the first imaging. For example, an absolute value (exposure dose) in ROI set with respect to a predetermined organ included in the imaged PET image is measured, and an exposure dose in other portions is estimated from the measured absolute value and the agent standard distribution map of the corresponding agent. Accordingly, the whole-body exposure dose can be estimated, thereby enabling to acquire the first information. Further, the first information acquired by such method can be memorized in association with each imaging condition to compile a database. By using this database, for example, the exposure dose of the subject by second imaging using the PET apparatus can be estimated from the first information matched with the imaging conditions of the second imaging or associated with similar imaging conditions.

In the embodiments described above, a case in which third information related to second imaging is displayed has been described; however, the embodiments are not limited thereto.

For example, the radiation dose management apparatus 300 can perform display of an exposure dose of a subject in various medical image diagnostic apparatuses such as the first medical image diagnostic apparatus 201 and the second medical image diagnostic apparatus 202. That is, the radiation dose management apparatus 300 can perform display of the exposure dose of the subject by omitting derivation of third information.

For example, the radiation dose management apparatus 300 acquires an exposure dose by imaging using the PET apparatus and an exposure dose by imaging using the X-ray CT apparatus, respectively, and displays the respective exposure doses on the display 302. For example, in a case where the first medical image diagnostic apparatus 201 illustrated in FIG. 13 is a PET apparatus, and the second medical image diagnostic apparatus 202 is an X-ray CT apparatus, the acquisition function 304a acquires information related to an exposure dose of a subject by a radioactive agent administered to the subject in an examination using the first medical image diagnostic apparatus 201 and information related to an exposure dose by the X-ray CT imaging performed with respect to the subject by using the second medical image diagnostic apparatus 202, respectively.

The information related to the exposure dose of the subject by the radioactive agent administered to the subject is also described as "first exposure dose information". The first exposure dose information can further include information related to an exposure dose of the subject by the radioactive agent administered to the subject in an examination using a PET apparatus and a SPECT apparatus other than the first medical image diagnostic apparatus 201, in addition to the information related to the exposure dose of the subject by the radioactive agent administered to the subject in an examination using the first medical image diagnostic apparatus 201.

Further, the information related to an exposure dose by radiation emitted to the subject is also described as "second exposure dose information". The second exposure dose information is information related to an exposure dose by the X-ray CT imaging performed with respect to the subject by using, for example, the second medical image diagnostic apparatus 202. The second exposure dose information can further include information related to an exposure dose by the X-ray CT imaging performed with respect to the subject by using another X-ray CT apparatus other than the second medical image diagnostic apparatus 202.

Figure 14:
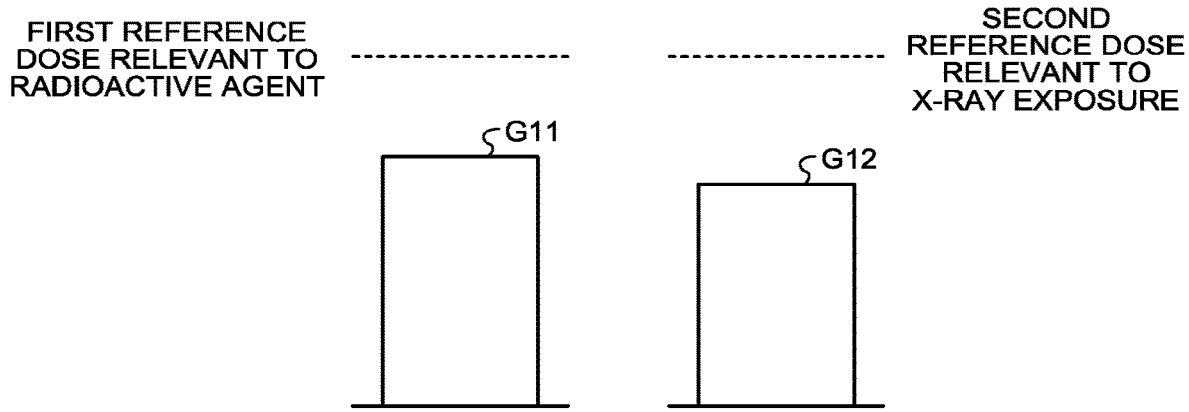
FIG. 14 is a diagram illustrating a display example of exposure dose information according to the other embodiment.

The control function 304b can display the first exposure dose information and the second exposure dose information on the display 302 in an arbitrary form. For example, the control function 304b displays the first exposure dose information and the second exposure dose information on the display 302 in a form of a graph, a numerical value, or a sentence. For example, as illustrated in FIG. 14, the control function 304b displays the first exposure dose information in a graph G11, and the second exposure dose information in a graph G12. FIG. 14 is a diagram illustrating a display example of exposure dose information according to the other embodiment.

Further, the control function 304b can display a reference dose with respect to the respective graphs based on information related to the reference dose (second information). For example, the control function 304b displays a first reference dose relevant to a radioactive agent by a dotted line on the graph G11 based on the first exposure dose information, as illustrated in FIG. 14. Here, the first reference dose is a radiation dose set by regulations or an academic society as an upper limit of the exposure dose by the radioactive agent. In other words, the control function 304b displays information indicating a differential dose between the first reference dose and an exposure dose indicated by the first exposure dose information. Accordingly, the operator can manage the exposure dose by the radioactive agent. Further, the operator can set conditions of imaging using the PET apparatus and a SPECT apparatus, while managing the exposure dose by the radioactive agent.

Further, for example, the control function 304b displays a second reference dose relevant to X-ray exposure by a dotted line on the graph G12 based on the second exposure dose information, as illustrated in FIG. 14. Here, the second reference dose is a radiation dose set by regulations or an academic society as an upper limit of the exposure dose by X-ray exposure. In other words, the control function 304b displays information indicating a differential dose between the second reference dose and an exposure dose indicated by the second exposure dose information. Accordingly, the operator can manage the exposure dose by X-ray exposure. Further, the operator can set conditions of X-ray CT imaging, while managing the exposure dose by X-ray exposure.

As the unit of the graph illustrated in FIG. 14, an arbitrary unit capable of evaluating the exposure dose can be used. Further, the unit of the graph G11 and the unit of the graph G12 may be different. The graph illustrated in FIG. 14 can be a graph indicating, for example, the percentage with respect to the reference dose. For example, the graph G11 can be a graph in which the exposure dose indicated by the first exposure dose information is converted to a percentage, by setting the first reference dose as "1000". Further, the graph G12 can be a graph in which the exposure dose indicated by the second exposure dose information is converted to a percentage, by setting the second reference dose as "1000".

Figure 15:
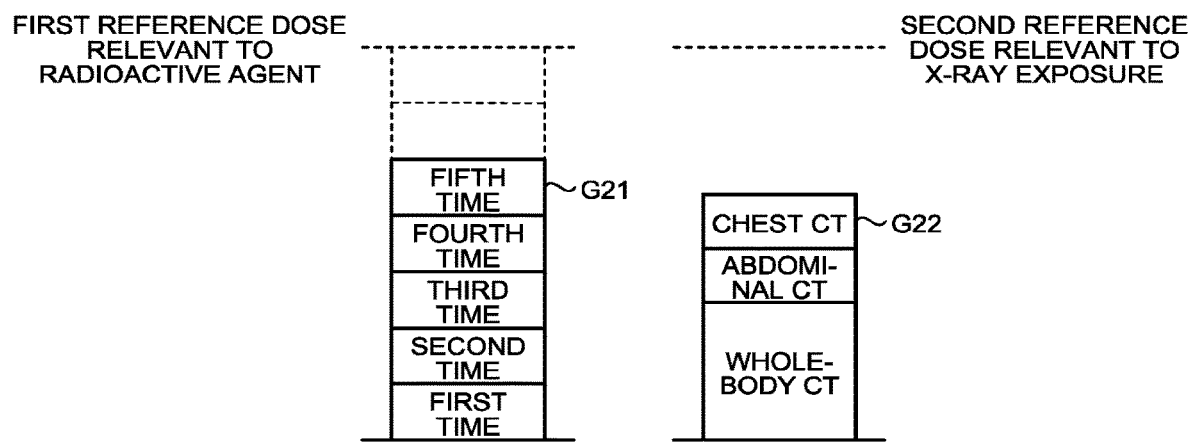
FIG. 15 is a diagram illustrating a display example of exposure dose information according to the other embodiment.

Here, there is a high possibility that the exposure dose when a radioactive agent is administered once has a similar value, although there is a variation due to the type and the amount of the radioactive agent. That is, the first exposure dose information related to the exposure dose of the subject by a radioactive agent administered to the subject can be displayed by the number of administration of the radioactive agent, as illustrated in a graph G21 in FIG. 15. Accordingly, the operator who referred to the graph G21 can easily ascertain how many more times of administration of the radioactive agent to the subject would exceed the reference dose. FIG. 15 is a diagram illustrating a display example of exposure dose information according to the other embodiment.

Further, the second exposure dose information related to the exposure dose by radiation emitted to the subject can be displayed by dividing the exposure dose for each X-ray CT imaging. As an example, the control function 304b can display the second exposure dose information by dividing the exposure dose information into an exposure dose by whole-body CT, an exposure dose by abdominal CT, and an exposure dose by chest CT. Accordingly, the operator who referred to a graph G22 can judge whether the reference dose is exceeded, taking into consideration the imaging conditions of the X-ray CT imaging. For example, the operator who referred to the graph G22 can judge that although there is a possibility that the reference dose is exceeded if further whole-body CT is performed, imaging can be performed without exceeding the reference dose in the case of the chest CT or the abdominal CT.

The second exposure dose information has been described above as the information related to the exposure dose by the X-ray CT imaging. However, the embodiment is not limited thereto. For example, the second exposure dose information can be information including an exposure dose by imaging using the X-ray diagnostic apparatus in addition to the exposure dose by the X-ray CT imaging. That is, the second exposure dose information can be also information related to the exposure dose by X rays applied to the subject.

Figure 16:
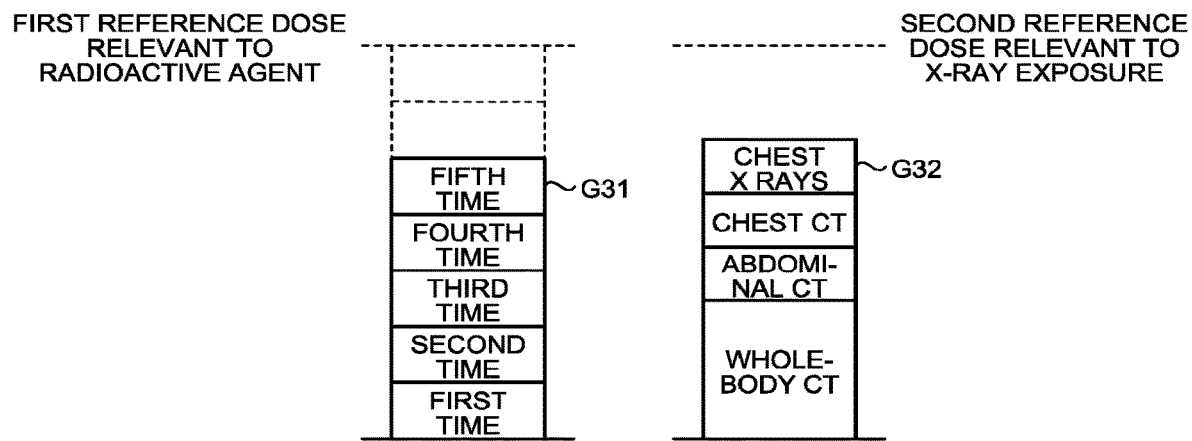
FIG. 16 is a diagram illustrating a display example of exposure dose information according to the other embodiment.

In this case, the control function 304b can display a graph G32 in which an exposure dose by the X-ray CT imaging (exposure dose by whole-body CT, abdominal CT, and chest CT) and an exposure dose by imaging using the X-ray diagnostic apparatus (exposure dose by chest X rays are added, for example, as illustrated in FIG. 16. Accordingly, the operator who referred to the graph G32 can accurately judge whether the second reference dose related to X-ray exposure is exceeded, taking into consideration the exposure dose by various types of modalities such as the X-ray CT apparatus and the X-ray diagnostic apparatus. FIG. 16 is a diagram illustrating a display example of exposure dose information according to the other embodiment.

In FIG. 14 to FIG. 16, one graph is displayed based on the first exposure dose information, and one graph is displayed based on the second exposure dose information. For example, in FIG. 16, a case in which a graph G31 of an exposure dose in an examination using a PET apparatus and a SPECT apparatus, and a graph G32 of an exposure dose in an examination using an X-ray CT apparatus and an X-ray diagnostic apparatus are displayed, has been described; however, the embodiment is not limited thereto. That is, the number of graphs to be displayed can be arbitrarily changed.

For example, the control function 304b can omit display of either one of the graph G11 and the graph G12 in FIG. 14. For example, the control function 304b can omit display of either one of the graph G21 and the graph G22 in FIG. 15. Further, for example, the control function 304b can omit display of either one of the graph G31 and the graph G32 in FIG. 16.

Figure 17:
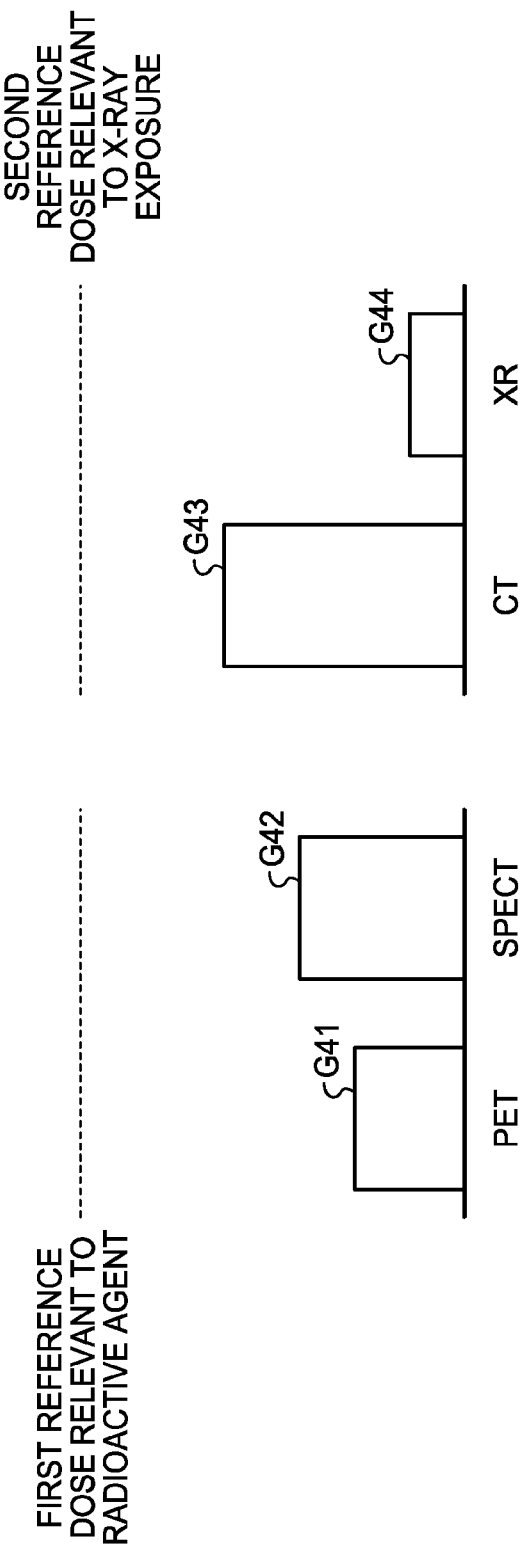
FIG. 17 is a diagram illustrating a display example of exposure dose information according to the other embodiment.

Further, the control function 304b can display a graph G41 indicating the exposure dose of a subject by a radioactive agent administered to the subject in an examination using a PET apparatus, and a graph G42 indicating the exposure dose of the subject by a radioactive agent administered to the subject in an examination using a SPECT apparatus, respectively, as illustrated in FIG. 17. That is, the control function 304b can display the first exposure dose information in two graphs of the graph G41 and the graph G42. FIG. 17 is a diagram illustrating a display example of exposure dose information according to the other embodiment.

Further, for example, the control function 304b can display a graph G43 indicating the exposure dose by X-ray CT imaging performed with respect to a subject by using an X-ray CT apparatus, and a graph G44 indicating the exposure dose by radiography performed with respect to the subject by using an X-ray diagnostic apparatus, respectively, as illustrated in FIG. 17. That is, the control function 304b can display the second exposure dose information in two graphs of the graph G43 and the graph G44.

The control function 304b can appropriately omit at least one display of the graph G41, the graph G42, the graph G43, and the graph G44 in FIG. 17.

Figure 18:
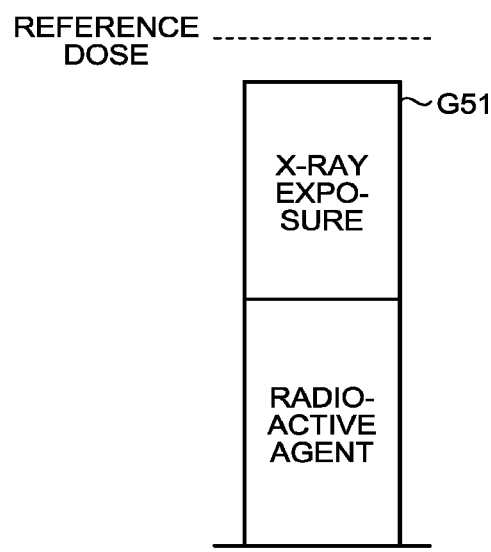
FIG. 18 is a diagram illustrating a display example of exposure dose information according to the other embodiment.

Further, the control function 304b can display a total dose of the exposure dose indicated by the first exposure dose information and the exposure dose indicated by the second exposure dose information as a graph G51. In this case, the control function 304b can display reference doses relevant to the radioactive agent and the X-ray exposure, instead of the first reference dose and the second reference dose, as illustrated in FIG. 18. The reference dose illustrated in FIG. 18 is a total value of, for example, the first reference dose and the second reference dose. In other words, the control function 304b displays information indicating a differential dose between the reference doses relevant to the radioactive agent and the X-ray radiation, and the total dose of the exposure dose indicated by the first reference dose information and the exposure dose indicated by the second reference dose information. Accordingly, the operator can integrally manage the exposure doses by the radioactive agent and the X-ray exposure. FIG. 18 is a diagram illustrating a display example of exposure dose information according to the other embodiment.

Figure 19:
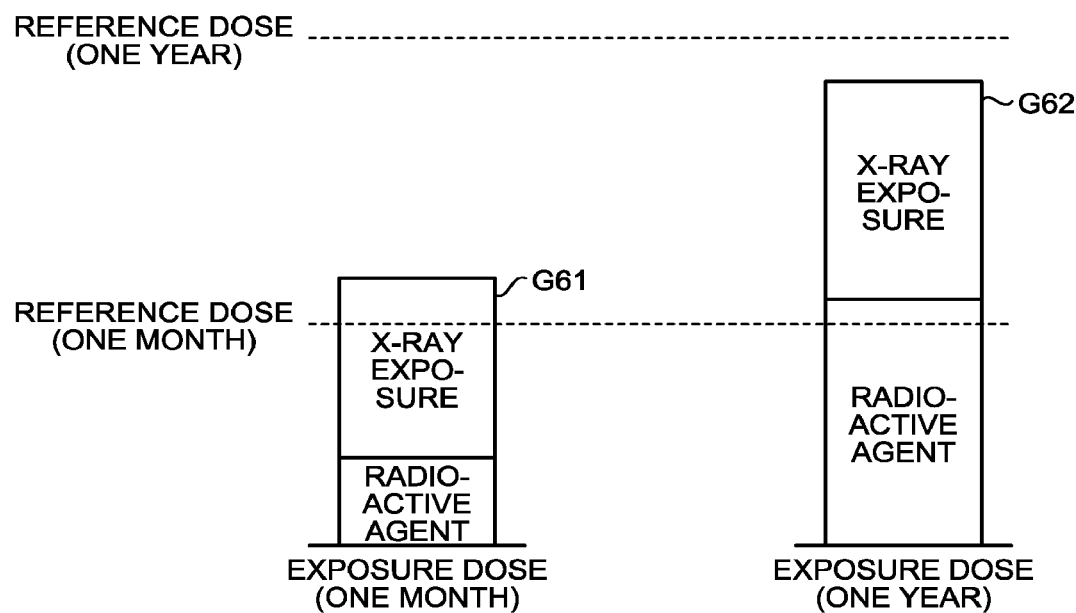
FIG. 19 is a diagram illustrating a display example of exposure dose information according to the other embodiment.

Further, the control function 304b can perform display corresponding to a set period. For example, when periods of "one month" and "one year" are set, the control function 304b displays a graph G61 indicating an exposure dose of a subject for the past one month, and a graph G62 indicating an exposure dose of the subject for the past one year, respectively, as illustrated in FIG. 19. The periods such as "one month" and "one year" can be arbitrarily set by the operator, or can be set by default. FIG. 19 is a diagram illustrating a display example of exposure dose information according to the other embodiment.

In a case illustrated in FIG. 19, the control function 304b displays a reference dose corresponding to a set period based on information related to a reference dose (second information). Specifically, the control function 304b displays a reference dose corresponding to "one month" and a reference dose corresponding to "one year", respectively. In other words, the control function 304b displays information indicating a differential dose between the reference dose corresponding to the set period, and the total dose of an exposure dose in the period indicated by the first reference dose information and an exposure dose in the period indicated by the second reference dose information. As illustrated in FIG. 19, the reference dose corresponding to "one year" may be different from a value obtained by simply multiplying the reference dose corresponding to "one month" by 12.

Further, FIG. 19 illustrates a case in which although the exposure dose of a subject for the past one year does not exceed the reference dose corresponding to "one year", the exposure dose of the subject for the past one month exceeds the reference dose corresponding to "one month". That is, even with the same exposure dose, there is a difference between a case where a subject is exposed with X rays in a concentrative manner in a short period and a case where the subject is exposed with X rays in a small amount for a long period, and the operator who referred to the display in FIG. 19 can manage the exposure dose of the subject more effectively.

The display in FIG. 19 is only an example, and for example, such a case that although an exposure dose of a subject for the past one month does not exceed the reference dose corresponding to "one month", the exposure dose of the subject for the past one year exceeds the reference dose corresponding to "one year" is also assumed.

Further, in FIG. 19, a period of the past one month and a period of the past one year have been described as an example of the set period. That is, in FIG. 19, a case where a period starting from the current time has been described; however, the embodiment is not limited thereto. For example, periods of "for one month", "for two months", and "for three months" can be set instead of the past one month.

Further, in FIG. 19, a case of displaying the total dose of the exposure dose indicated by the first exposure dose information and the exposure dose indicated by the second exposure dose information has been described. However, similarly to the case illustrated in FIG. 14 to FIG. 17, the exposure dose indicated by the first exposure dose information and the exposure dose indicated by the second exposure dose information can be respectively displayed. That is, the control function 304b can display information indicating a differential dose between the first reference dose corresponding to the set period and the exposure dose indicated by the first exposure dose information, and information indicating a differential dose between the second reference dose corresponding to the set period and the exposure dose indicated by the second exposure dose information, respectively.

Further, it has been described that the display of from FIG. 14 to FIG. 19 is performed by the radiation dose management apparatus 300; however, the embodiment is not limited thereto. For example, the first medical image diagnostic apparatus 201 or the second medical image diagnostic apparatus 202 can perform the display of FIG. 14 to FIG. 19, instead of the radiation dose management apparatus 300.

The term "processor" used in the above descriptions represents, for example, a CPU (Central Processing Unit), a GPU (Graphics Processing Unit), or a circuit such as an Application Specific Integrated Circuit (ASIC) and a programmable logic device (for example, a Simple Programmable Logic Device (SPLD), a Complex Programmable Logic Device (CPLD), and a Field Programmable Gate Array (FPGA)). The processor realizes its functions by reading out and executing a program stored in a memory. Instead of storing a program in a memory, it is also possible to directly incorporate a program in the circuit of a processor. In this case, the processor realizes its functions by reading out and executing the program incorporated in the circuit of the processor. Further, the respective processors in the embodiments described above are not limited to those configured as a single circuit, and it is also possible to configure the processor as a single processor by combining a plurality of independent circuits to realize its functions. Further, it is possible to integrate a plurality of constituent elements in FIG. 2 in one processor to realize its functions.

In the above descriptions of the embodiments, the respective constituent elements of the respective device illustrated in the drawings are functionally conceptual and are not necessarily physically configured as in the drawings. That is, a specific mode of dispersion and integration of the respective device is not limited to the illustrated ones, and all or a part thereof may be functionally or physically distributed or integrated in an optional unit, according to various kinds of loads and the status of use. All or an optional part of the various processing functions performed by the respective device can be realized by a CPU or a program analyzed and executed by the CPU, or can be realized as hardware by a wired logic.

The control method described in the above embodiments can be realized by executing a control program prepared in advance by a computer such as a personal computer and a workstation. This control program can be distributed via a network such as the Internet. Further, this control program can be executed while it is recorded in a computer-readable recording medium such as a hard disk, a flexible disk (FD), a CD-ROM, an MO, and a DVD and read therefrom by a computer.

According to at least one of the embodiments described above, it is possible to manage the dose of radiation caused by a plurality of medical image diagnostic apparatuses.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic system including a first medical radiopharmaceutical image diagnostic apparatus and a second medical image diagnostic apparatus, and comprising:
    processing circuitry configured to
        acquire first information related to an exposure dose of a subject from a radiopharmaceutical agent administered to the subject for imaging conducted by the first medical image diagnostic apparatus, and
        display reference information for determining imaging conditions of X-ray CT imaging conducted by the second medical image diagnostic apparatus to be performed with respect to the subject on a display, based on the first information and second information related to a reference dose.

2. The medical image diagnostic system according to claim 1, wherein the processing circuitry is configured to acquire the first information related to the exposure dose of the radiopharmaceutical agent for each organ.

3. The medical image diagnostic system according to claim 1, wherein the processing circuitry is configured to acquire the first information related to the exposure dose of the subject, taking into consideration an accumulation degree and an influence rate of the radiopharmaceutical agent for each organ.

4. The medial image diagnostic system according to claim 3, wherein the first information is information on each organ.

5. The medical image diagnostic system according to claim 3, wherein the first information is information of a whole-body exposure dose acquired by adding a weighted accumulation degree acquired by weighting the accumulation degree by the influence rate for a plurality of organs.

6. The medical image diagnostic system according to claim 3, wherein the accumulation degree and the influence rate correspond to a type of the radiopharmaceutical agent.

7. The medical image diagnostic system according to claim 1, wherein when a total dose of an exposure dose indicated by the first information and an exposure dose of the subject by the X-ray CT imaging estimated from imaging conditions of the X-ray CT imaging exceeds a reference dose indicated by the second information, the processing circuitry is configured to display warning information indicating that the total dose exceeds the reference dose on the display as the reference information.

8. The medical image diagnostic system according to claim 1, wherein when a total dose of an exposure dose indicated by the first information and an exposure dose of the subject by the X-ray CT imaging estimated from imaging conditions of the X-ray CT imaging exceeds a reference dose indicated by the second information, the processing circuitry is configured to display request information for requesting reception of an operator's approval on the display as the reference information.

9. The medical image diagnostic system according to claim 1, wherein when a total dose of an exposure dose indicated by the first information and an exposure dose of the subject by the X-ray CT imaging estimated from imaging conditions of the X-ray CT imaging exceeds a reference dose indicated by the second information, the processing circuitry is configured to display recommendation information recommending a change of set imaging conditions of the X-ray CT imaging on the display as the reference information.

10. The medical image diagnostic system according to claim 9, wherein the processing circuitry is further configured to change imaging conditions of the X-ray CT imaging based on a parameter relevant to image quality input via an input interface.

11. The medical image diagnostic system according to claim 1, wherein the processing circuitry is configured to display a reference image predicting an image acquired by set imaging conditions of the X-ray CT imaging on the display as the reference information.

12. The medical image diagnostic system according to claim 1, wherein the processing circuitry is configured to display information indicating a differential dose between a reference dose indicated by the second information and an exposure dose indicated by the first information on the display as the reference information.

13. The medical image diagnostic system according to claim 1, wherein when an exposure dose indicated by the first information exceeds an allowed radiation dose indicated by the second information, the processing circuitry is configured to display warning information indicating that the radiation dose exceeds an allowed radiation dose to the subject on the display as the reference information, before accepting imaging conditions of the X-ray CT imaging.

14. The medical image diagnostic system according to claim 13, wherein when the exposure dose indicated by the first information exceeds the allowed radiation dose indicated by the second information, the processing circuitry is configured to display request information for requesting reception of an operator's approval on the display as the reference information.

15. A medical image diagnostic system including a first medical image diagnostic apparatus related to radiation and a second medical image diagnostic apparatus related to radiation, and comprising:
processing circuitry configured to
acquire first information related to an exposure dose by X-ray CT imaging conducted by the first medical image diagnostic apparatus performed with respect to a subject, and
display reference information relevant to a radiopharmaceutical agent to be administered to the subject on a display for imaging conducted by the second medical image diagnostic apparatus, based on the first information and second information related to a reference dose.

16. A radiation dose management apparatus comprising:
processing circuitry configured to
acquire first exposure dose information related to an exposure dose of a subject from a radiopharmaceutical agent administered to the subject for imaging conducted by a first medical image diagnostic apparatus, and second exposure dose information related to an exposure dose by X-ray CT imaging conducted by a second medical image diagnostic apparatus performed with respect to the subject, and
display the first exposure dose information and the second exposure dose information on a display.

17. The radiation dose management apparatus according to claim 16, wherein the processing circuitry is configured to display information indicating a differential dose between reference doses relevant to a radiopharmaceutical agent and X-ray exposure and a total dose of an exposure dose indicated by the first exposure dose information and an exposure dose indicated by the second exposure dose information, on the display based on the information related to the reference dose.

18. The radiation dose management apparatus according to claim 17, wherein the processing circuitry is configured to display information indicating a differential dose between a reference dose corresponding to a set period, and a total dose of an exposure dose in the period indicated by the first exposure dose information and an exposure dose in the period indicated by the second exposure dose information, on the display based on the information related to the reference dose.

19. The radiation dose management apparatus according to claim 16, wherein the processing circuitry is configured to display information indicating a differential dose between a first reference dose relevant to the radiopharmaceutical agent and the exposure dose indicated by the first exposure dose information, and information indicating a differential dose between a second reference dose relevant to X-ray exposure and the exposure dose indicated by the second exposure dose information, on the display based on the information related to the reference dose.

20. The radiation dose management apparatus according to claim 19, wherein the processing circuitry is configured to display information indicating a differential dose between the first reference dose corresponding to a set period and the exposure dose indicated by the first exposure dose information, and information indicating a differential dose between the second reference dose corresponding to the period and the exposure dose indicated by the second exposure dose information, on the display based on the information related to the reference dose.

21. The medical image diagnostic system according to claim 1, wherein the first medical image diagnostic apparatus is a PET apparatus or a SPECT apparatus.

\* \* \* \* \*